United States Patent [19]

Werschmidt et al.

[11] Patent Number: 5,620,427
[45] Date of Patent: Apr. 15, 1997

[54] LUER LOCK SYSTEM

[75] Inventors: Gary S. Werschmidt, Yorba Linda; Raymond P. Feith, Rialto, both of Calif.; David R. Kipp, 2371 Edna Way, Upland, Calif. 91784

[73] Assignee: David R. Kipp, Upland, Calif.

[21] Appl. No.: 431,073

[22] Filed: Apr. 27, 1995

[51] Int. Cl.$^6$ ........................................ A61M 25/00
[52] U.S. Cl. ........................ 604/283; 137/516.13
[58] Field of Search ......................... 604/283, 280, 604/240–243, 103, 33–34, 249, 256, 257; 285/330, 332, 397–398, 242; 137/516.13; 138/109, 89

[56]  References Cited

U.S. PATENT DOCUMENTS

| | | |
|---|---|---|
| 4,346,703 | 8/1982 | Dennehey et al. . |
| 4,439,188 | 3/1984 | Dennehey et al. . |
| 4,607,868 | 8/1986 | Harvey et al. . |
| 4,778,447 | 10/1988 | Velde et al. . |
| 4,880,414 | 11/1989 | Whipple . |
| 4,963,133 | 10/1990 | Whipple . |
| 4,991,629 | 2/1991 | Ernesto et al. . |
| 5,125,915 | 6/1992 | Berry et al. . |
| 5,215,538 | 6/1993 | Larkin . |
| 5,456,676 | 10/1995 | Nelson et al. . |

Primary Examiner—Corrine M. McDermott
Assistant Examiner—Perry E. Van Over
Attorney, Agent, or Firm—Richard L. Myers

[57]  ABSTRACT

An improved luer lock connector having a pair of tapered engagement surfaces between the hub and one of the two components of the luer connector. The tapered engagement surfaces provide a gradual frictional engagement when tightening the hub to minimize inadvertent reverse rotation and loosening of the hub. The tubular body is also provided with a plurality of axially extending splines for engagement with a plurality of inwardly radially directed ribs on the hub to positively rotationally lock the two components when the hub is in a proximal position. A small circumferential ridge provides tactile feedback to an operator to indicate when the hub is in a positive rotationally interlocked relationship with the tubular body. The hub may be completely removed in a proximal direction from the tubular body and retracted proximally along a supply line to remove it from the connector site.

32 Claims, 12 Drawing Sheets

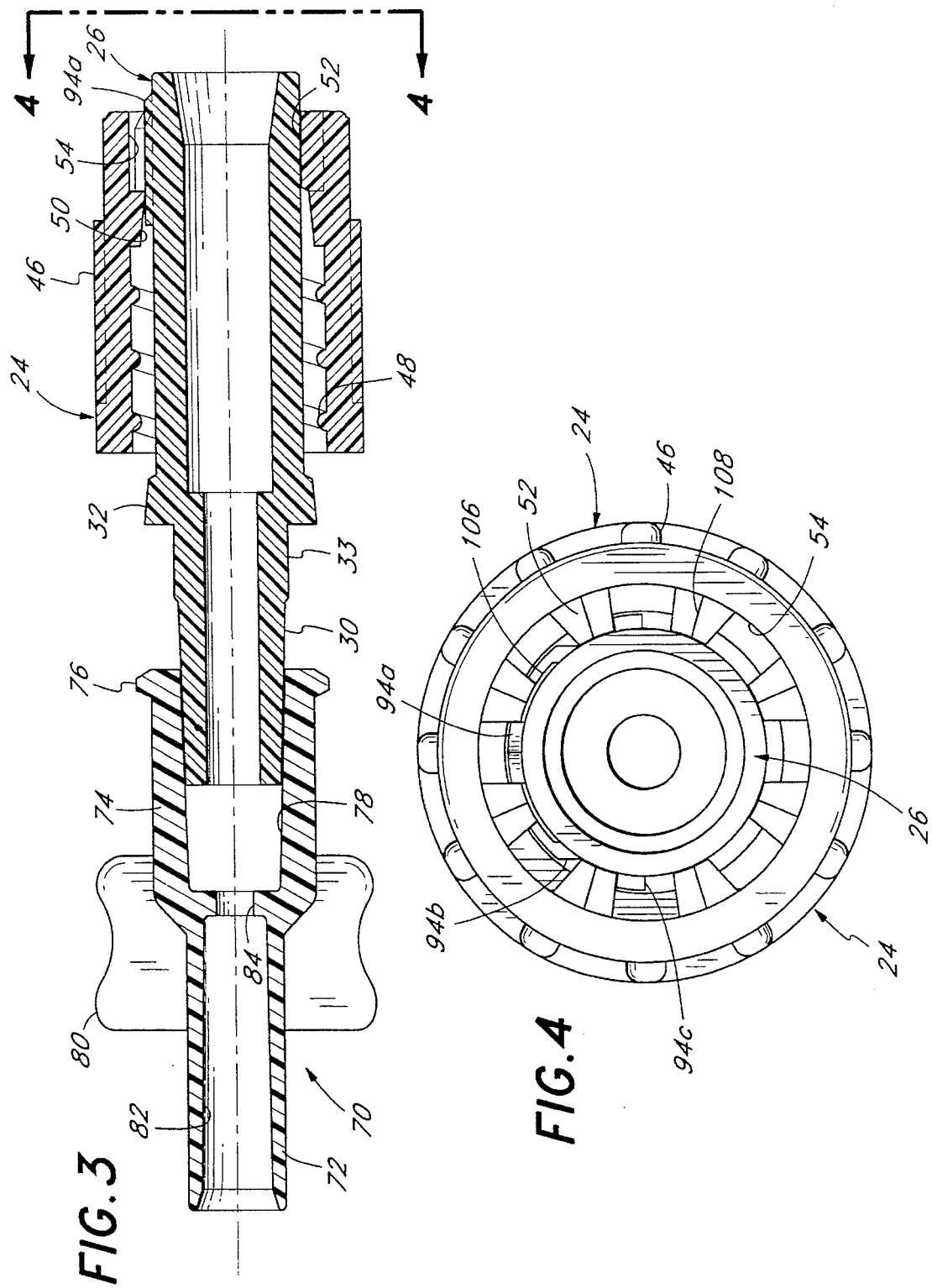

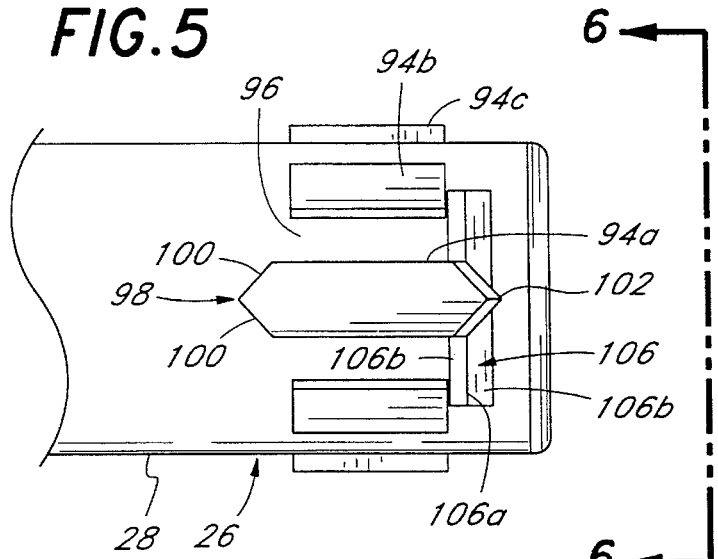
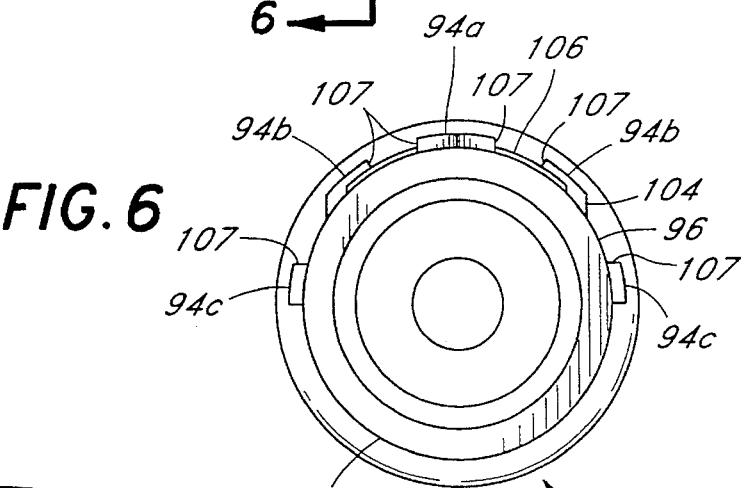
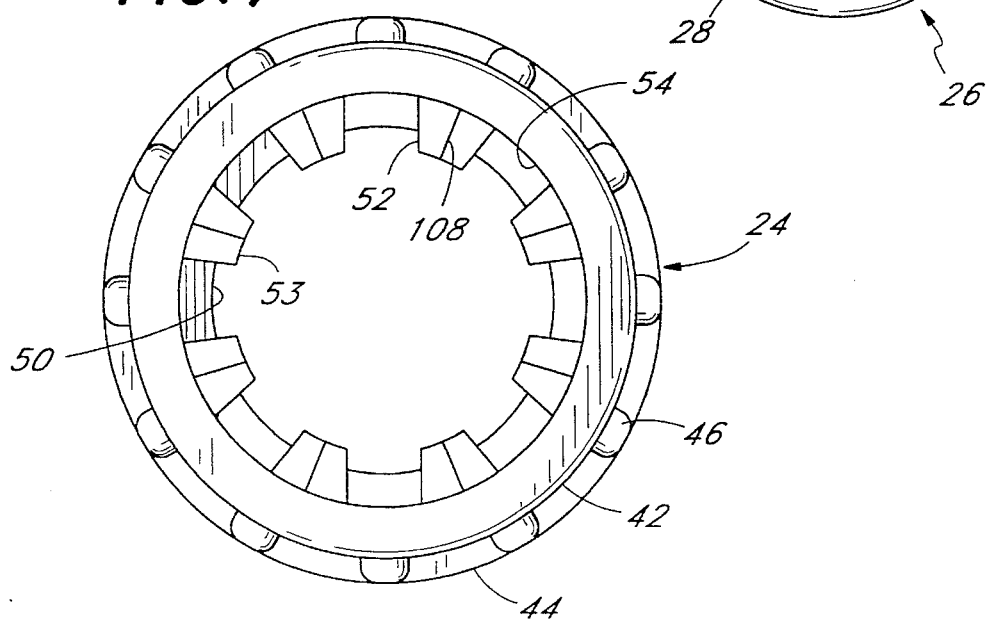

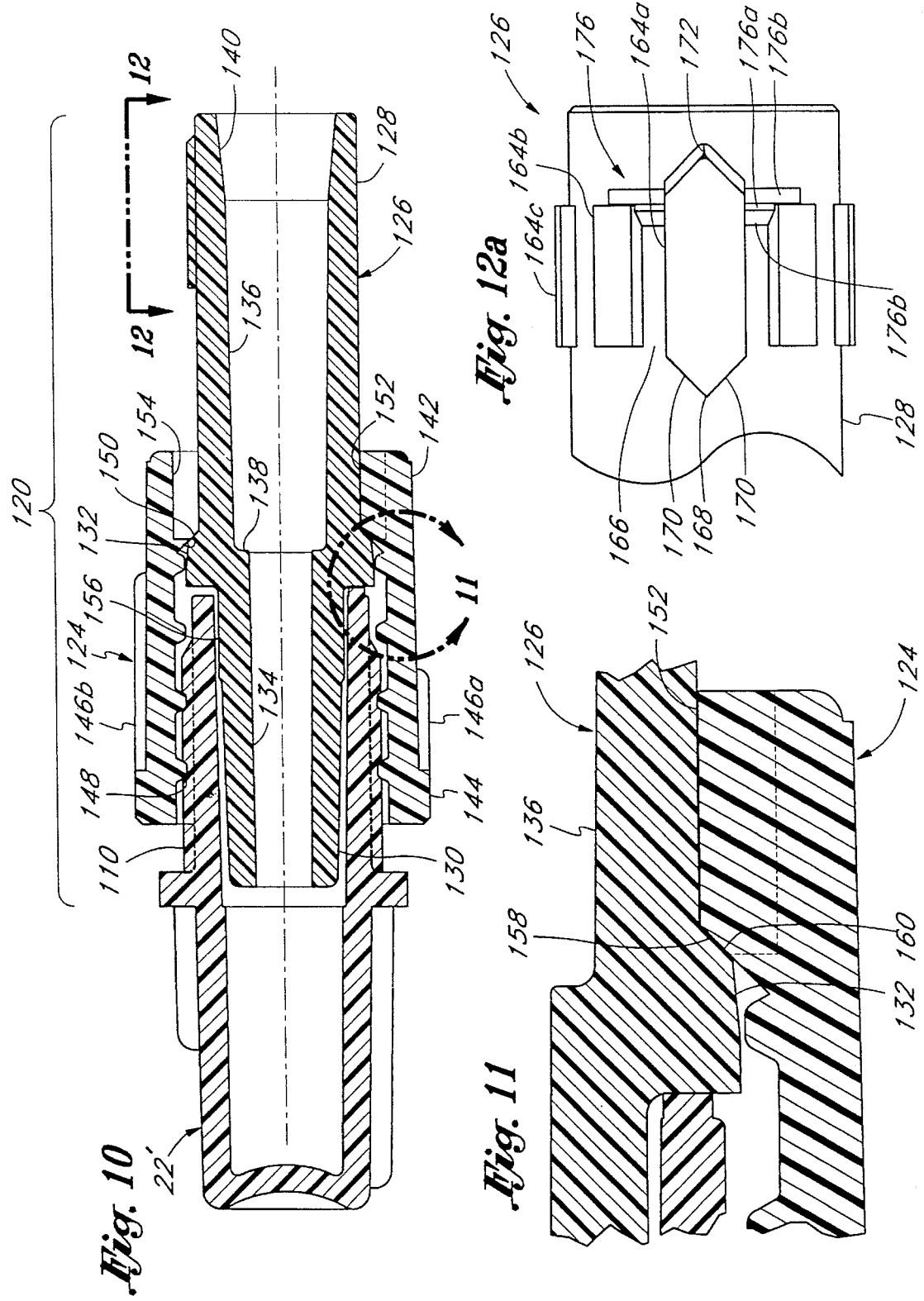

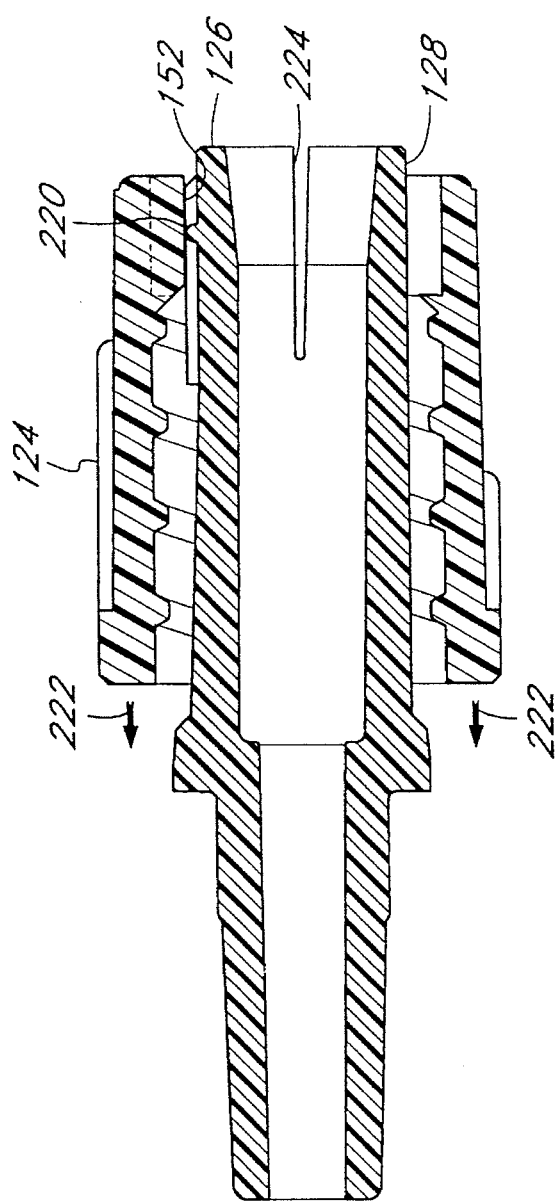
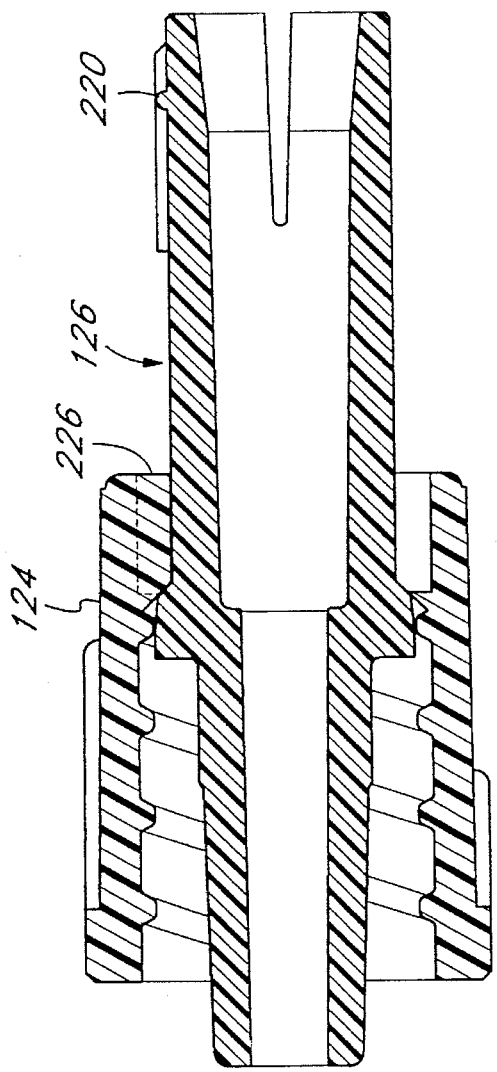
Fig. 14a
Fig. 14b

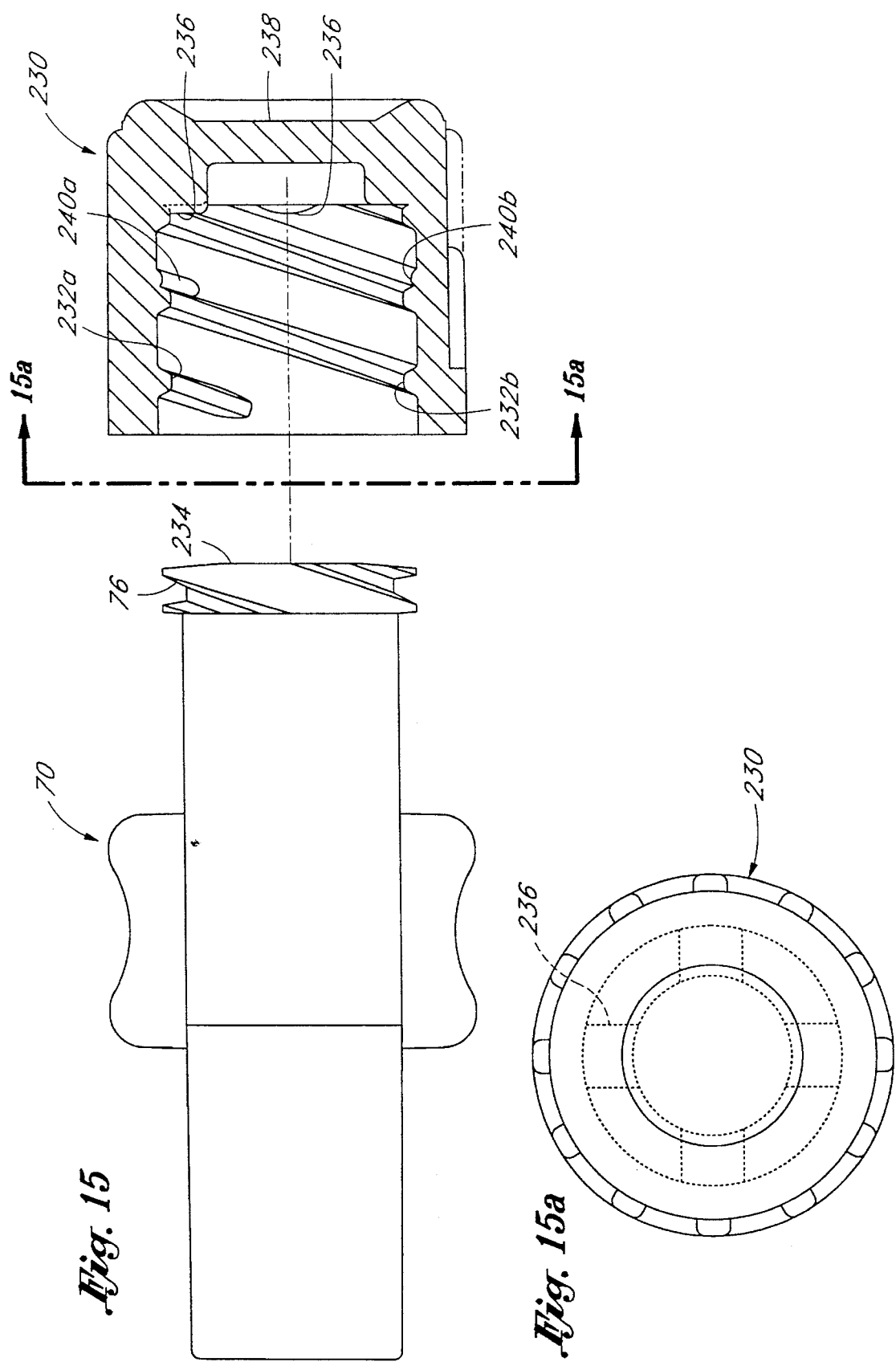

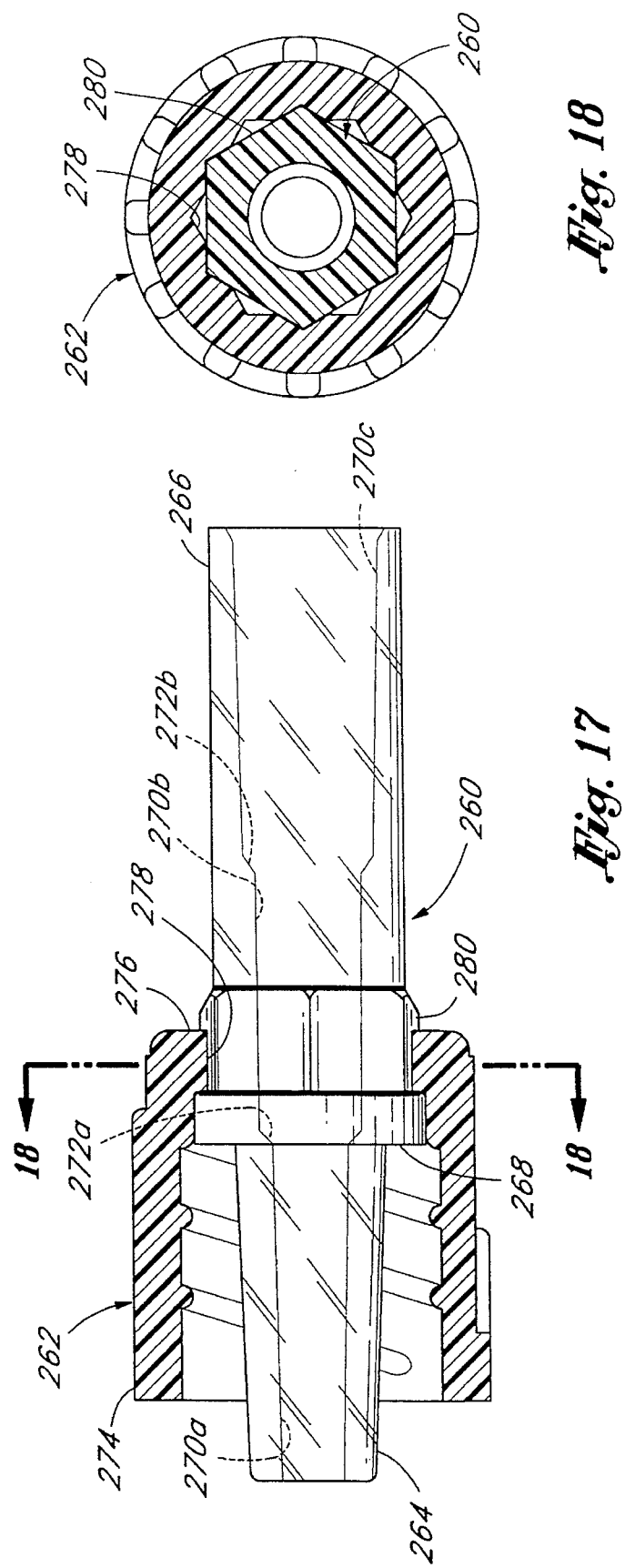

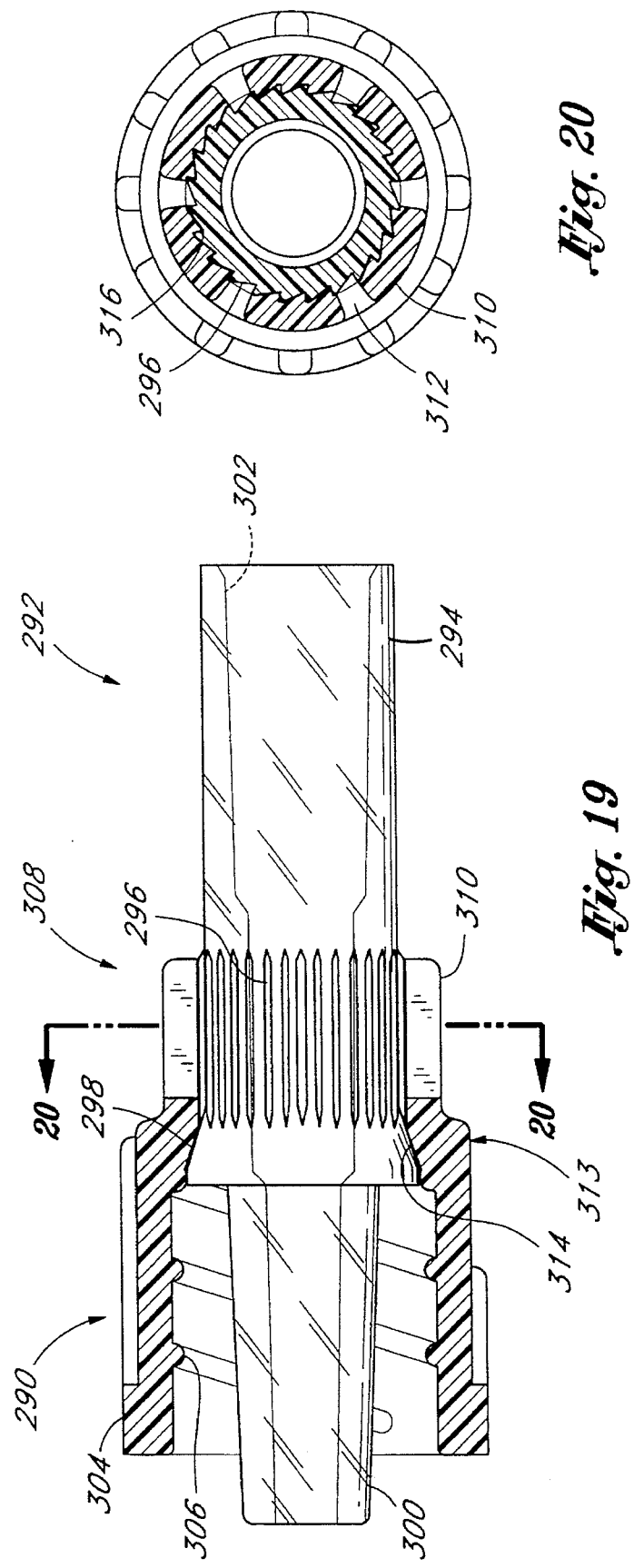

LUER LOCK SYSTEM

FIELD OF THE INVENTION

The present invention pertains to a luer-lock connector system for medical devices and, more particularly, to a luer-lock connector having male and female luer components adapted to engage one another with the assistance of a hub, and a mating engagement between the hub and male luer component to facilitate disengagement of the luer-lock connector.

BACKGROUND OF THE INVENTION

Medical connectors for intravenous applications often utilize standard luer connectors having a tapered tubular body which fits into a tapered socket or luer adaptor of a second body to provide a frictional seal between two fluid conduits.

In the early embodiments, the luer connector includes a tapered male nose portion adapted to fit within a tapered female receiver, the two pieces being locked together with a threaded hub engagement. The hub was typically rotationally coupled to the male portion so that assembling the luer connector together by twisting the hub resulted in twisting of the male portion, sometimes establishing a reverse torque within one or both of the fluid conduits extending from the connector components. This reverse torque tended to twist the fluid conduits connected to one or both of the connector components which can cause the loss of patency of the IV site, or other complications associated with twisted conduits.

To remedy this situation, the next generation of luer locks incorporated a separate rotatable hub or sleeve having internal ribs for mating with external splines on either the male or female luer connector body. The hub typically slides axially and freely spins over a first one of the luer components and has an internal stop which cooperates with an external stop on the first luer component. When the male and female components are brought together, the hub engages an external projection or thread on the second luer component and, due to the engaging stops, urges the male component into sealing engagement with the female component. Prior hubs assemble onto the male component from the nose or distal end, and are forced over a stop ring or other structure on the tubular male component. Jamming the hub onto the male component in this manner often results in hoop stress fractures of either piece.

The hub on this type of connector may have two axial positions: a distal, freely rotatable position which allows relative hub to first luer component rotation, and a proximal position in which the hub and first luer component are rotationally locked. This rotational coupling is typically provided by internal ribs on the hub engaging projections on the exterior surface of the first luer component when the hub is in the proximal position. See, e.g., U.S. Pat. No. 4,607,868 to Harvey et al. The rotational lock is provided to assist in breaking the luer connection between the tapered male and female surfaces. Indeed, some luer connections are left in place for extended periods of time resulting in the male and female surfaces of the luer connection being essentially glued together.

Although the hub in the prior art connectors is tightened to join the male and female components together, the hub has a tendency to rotate in a reverse direction increasing the risk of disengagement of the medication line. To prevent this from happening, nurses sometimes apply tape over a tightened hub to prevent it from rotating relative to the male and female luer connection.

Another problem with the aforementioned hub-type luer connection arises from the internal ribs on the hub and the external projections on the first luer component to provide rotational locking engagement. The operator occasionally has difficulty sliding the hub proximally over the first luer component to engage the projections because the ribs and projections are circumferentially aligned and in some rotational positions interfere with each other. In addition, the outer diameter of the hub is large enough to interfere with the appropriate percutaneous entrance angle for an I.V. needle, particularly in pediatric applications. The use of hub-type luer connectors on these sensitive applications may be inappropriate, and a simple slip luer is commonly used. This necessitates maintaining an inventory of both types of luer connectors.

Thus there is a need for an improved connector in which the risk of inadvertent hub rotation is minimized by a relatively high anti-rotation friction, and the other limitations of the prior art connectors are overcome. There is also a need for a connector in which the hub can be pulled away from the luer to permit slip connections.

SUMMARY OF THE INVENTION

The present invention provides a medical connector, including an elongate tubular body having a central lumen extending axially therethrough, and a hub movable axially over the tubular body. The hub and tubular body include frictional engagement surfaces which cooperate to resist rotation of the hub with respect to the tubular body when the medical connector is assembled. More specifically, the hub is movable between a proximal position in which the hub is rotationally locked with respect to the tubular body, and a distal position in which the frictional engagement surfaces contact each other to resist relative rotation of the hub and tubular body. When the hub is at an intermediate position, in between the proximal and distal positions, the hub is freely rotatable about the tubular body.

The tubular body includes at least one radially outwardly extending projection which mates with an axially extending channel on the interior surface of the hub so that the hub is rotationally locked but remains axially movable with respect to the tubular body when the projection is within the channel. This corresponds to the proximal position of the hub over the tubular body. Preferably, five projections are provided, to minimize the occurrence of rotational skipping of the hub with respect to the tubular body. All of the projections are preferably positioned within a single hemisphere (side) of the tubular body to facilitate manufacturing.

In a preferred form, the frictional engagement surfaces comprise inclined annular surfaces; one around the exterior of the tubular body and one within the interior of the hub. Both these annular surfaces are preferably inclined radially outward in the distal direction, the inclination being within the range of from about 1% to about 15% with respect to the longitudinal axis of the tubular body. The tapered engagement surfaces are configured so that the hub can be positioned at a first distal position where the engagement surfaces are in contact, and then can be moved to a second distal position disposed distally from the first distal position. The amount of axial movement of the hub from the first distal position to the second distal position determines the level of frictional engagement between the engaging surfaces.

In accordance with the present invention, a preferred luer lock connector includes a first tubular body having a tapered nose portion which fits within a tapered recess of a second tubular body. The connector also includes a hub axially slidable over the first tubular body. Optimally, the hub is slidable over the proximal end of the first tubular body. The hub preferably includes one or more interior threads within a distal region which mate with one or more exterior thread segments on the second tubular body. The hub and first tubular body include mating engagement surfaces causing the hub to urge the first tubular body toward the second tubular body when the internal threads engage the external thread segment. The cooperating engagement surfaces comprise annular surfaces which are inclined radially outwardly toward the second tubular body. The engagement surfaces are inclined at a shallow angle so that the hub can travel further toward the second tubular body after initial contact between the surfaces. This additional travel ensures a good frictional engagement between the surfaces resisting further rotation of the hub with respect to the first tubular body.

Furthermore, the first tubular body includes axial splines on the proximal end opposite the tapered nose which cooperate with axial channels formed on the interior of the hub. The hub can be slid axially along the tubular body into a position wherein the splines engage the channel so that the two components are rotationally locked together. A plurality of radially inwardly directed ribs are formed on the hub between the channels. At least one of the axial splines on the first tubular body includes a cam surface for rotationally directing the inwardly directed ribs between the axial splines. The first tubular body further includes a circumferential ridge in proximity with the axial splines which interferes with the movement of the inwardly directed ribs to indicate when the ribs are registered with the axial splines, thus rotationally coupling the hub to the first tubular body. Finally, the hub can be moved proximally past the circumferential ridge and completely removed from contact with the first tubular body, when a locking hub is not desired.

BRIEF DESCRIPTION OF THE DRAWINGS

FIG. 3 is a cross-sectional view similar to FIG. 2 with the hub shown in a proximal position in which the hub is rotationally coupled to a male luer component;

FIG. 4 is an end elevational view of the two-piece luer-lock connector taken along line 4—4 of FIG. 3;

FIG. 5 is a partial plan view of a proximal end of the male luer component as seen along line 5—5 of FIG. 2;

FIG. 6 is an end elevational view of the male luer component taken along line 6—6 of FIG. 5;

FIG. 7 is an end elevational view of the hub of the two-piece luer-lock connector;

FIG. 10 is a cross-sectional view of another two-piece luer lock connector and protector cap embodiment;

FIG. 11 is a detailed view of an area of engagement between a male luer component and rotatable hub shown in FIG. 10;

FIG. 12a is a partial plan view of a proximal end of the male luer component showing a spline arrangement as seen along line 12—12 of FIG. 10;

FIG. 14a is a cross-sectional view of a hub advancing distally over an alternative luer component;

FIG. 14b shows the hub advanced distally onto the male luer component of FIG. 14a;

FIG. 15 is an exploded view of a female luer component and a protective cap therefor;

FIG. 15a is an elevational view of the protective cap for the female luer component taken along 15a—15a of FIG. 15;

FIG. 17 is a cross-sectional view of a two-piece luer-lock connector having a hex coupling between the hub and male component;

FIG. 18 is a cross-sectional view of the hex coupling taken along line 18—18 of FIG. 17;

FIG. 19 is a cross-sectional view of a two-piece luer-lock connector having a ratchet coupling between the hub and male component; and FIG. 20 is a cross-sectional view of the ratchet coupling taken along line 20—20 of FIG. 19.

DETAILED DESCRIPTION OF THE PREFERRED EMBODIMENTS

Figures 1, 2:
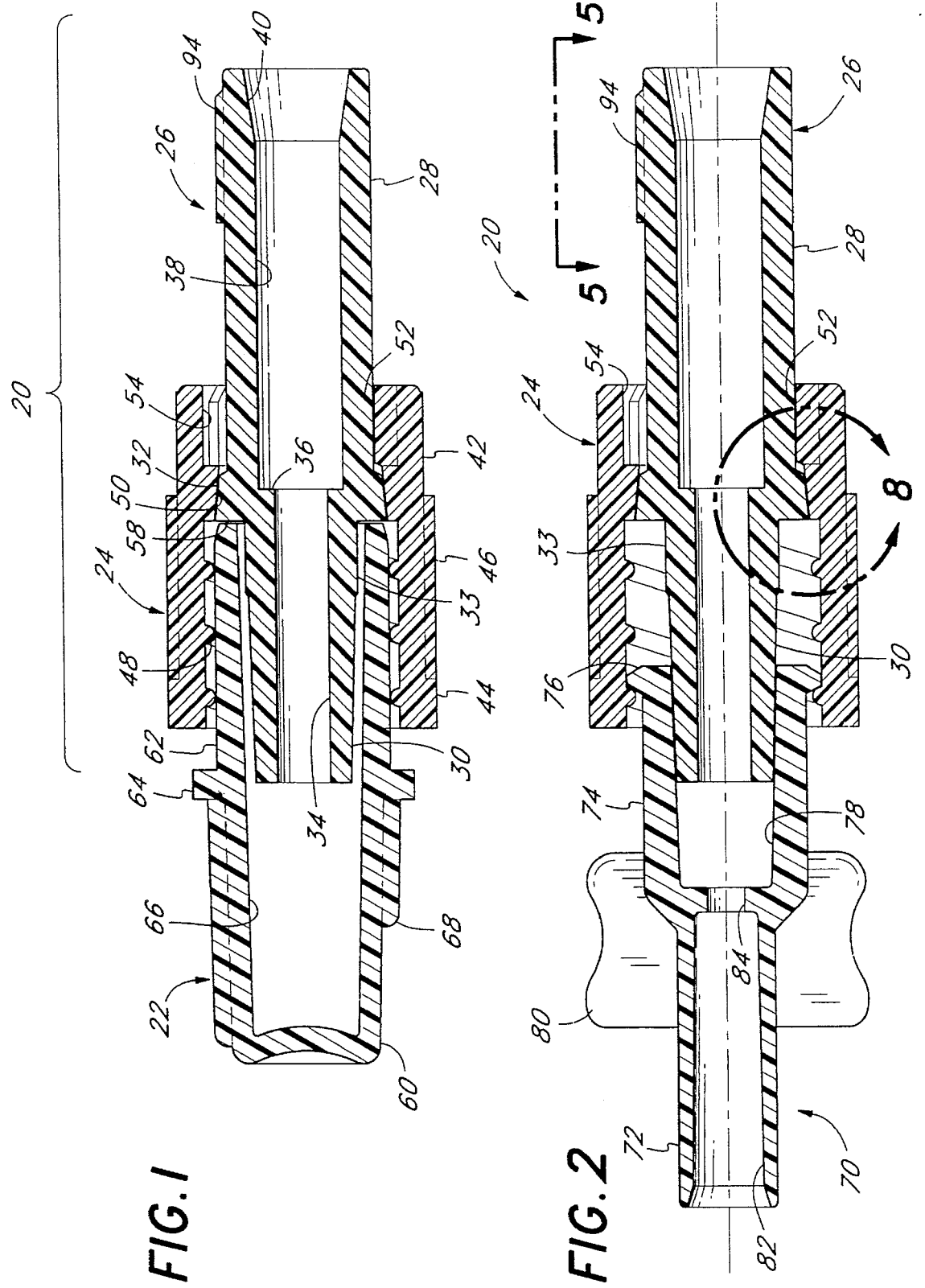
FIG. 1 is a cross-sectional view of a two-piece luer-lock connector and protector cap.
FIG. 2 is a cross-sectional view of the two-piece luer-lock connector engaged with a female luer component and showing a hub in the distal, anti-rotation position.

FIG. 1 is a cross-sectional view showing a two-piece medical luer-lock connector 20 engaged by a protector cap 22. The two-piece luer-lock connector comprises a hub 24 and a tubular male luer component 26. Although the present invention will be described in terms of the two-piece luer-lock connector 20 comprising a hub and male luer connector, the hub could also be associated with a female luer connector, as will be readily apparent to one of skill in the art. In most cases, however, the hub 24 is associated with a proximal component of a luer connector, the proximal direction being away from the patient or application site. One particularly useful application for the present invention is for attaching an intravenous fluid supply line to an IV catheter at an infusion site.

In the illustrated embodiment, the male luer component 26 comprises an elongate tubular body having a proximal tubular section 28, a tapered nose 30, and a tapered shoulder 32 disposed therebetween. A cylindrical step 33 is provided on the tapered nose 30 just distal from the tapered shoulder 32. A central lumen consists of a distal conduit 34 transitioning at a step 36 to a proximal conduit 38. The proximal conduit 38 terminates in a flared mouth 40 for receiving a flexible delivery hose (not shown) which may be inserted all the way to the stop 36 and glued or otherwise adhered into place.

The hub 24 comprises a generally tubular sleeve having a proximal cylindrical exterior surface 42, a distal annular flange 44, and a series of axially extending grip rails 46, as best seen in FIG. 7. The hub 24 has three distinct interior surface regions. A first distal region includes single or multiple internal threads 48. The internal threads 48 may be standard ISO threads or may comprise helical grooves termed sometimes "oversized threads." The proximal end of the distal region terminates at an anti-rotational friction enhancing structure such as an annular internal ramp 50. Finally, a proximal region includes a plurality of radially, inwardly directed ribs 52 separated by channels 54. The functions of the internal surfaces of the hub 24 will be described more fully below.

Male Luer Component Breather Cap

The present invention is preferably provided prior to use with a protector cap 22. As seen on an alternative cap 22' in FIG. 9, cap 22 includes a plurality of end projections 56 which create a gap 58 (see FIG. 1) between the protector cap 22 and the male luer component 26 for ease of priming the device when the cap is in place, the small gap presenting a tortuous path for bacteria after sterilization. More particularly, the protector cap 22 is defined by a closed end portion 60 and an engagement tube portion 62 separated by an annular flange 64 which helps to prevent contamination of the tortuous path. An interior wall 66 is tapered at approximately the same angle as the tapered nose 30 of the male component 26. In one embodiment, the interior wall 66 is formed with a draft of approximately 1° with respect to a central axis, while the nose 30 has a total taper of 0.060 in/in, which corresponds to an angle of 1.7° adjacent the interior wall 66. The outer diameter of the engagement tube 62 is slightly greater than the inner diameter of the internal threads 48 of the hub 24. Thus, when the cap 22 is inserted around the tapered nose 30 and within the hub 24, it is frictionally engaged by the internal threads 48 and protects the nose. Further, the end projections 56 create the aforementioned gap 58 to allow the passage of sterilization gas or other media. The protector cap 22 additionally has a plurality of axially extending grip rails 68 for facilitating the removal from the two-piece luer-lock connector 20.

In certain embodiments, the hub 24 is eliminated and an alternative protector cap is used which has a smaller internal diameter for interfering with the step 33 on the tapered nose 30. In this alternative embodiment, the inner circumference of the protective cap may have inwardly directed ribs for interfering with the step 33, or, the step 33 may be formed with a plurality of separate ribs for interfering with a continuous inner diameter of the protective cap.

In all of the protective cap embodiments, a small tortuous passage is provided through the inner lumen of the male component 26 and around the proximal end of the protective cap 22 by virtue of the end projections 56 and gap 58. Thus, the assembled male component 26 and protective cap 22 can be sterilized allowing gases to flow therebetween. However, after sterilization, an open, yet highly tortuous path is provided between the protective cap 22 and inner lumen of the male component 26. This tortuous path helps prevent contamination of the male luer component 26.

Luer-Lock Connector

Now with reference to FIGS. 2 and 3, the two-piece luer-lock connector 20 is shown coupled to a second tubular body, in this case a female luer component 70. Luer component 70 may provide communication with a segment of IV line, medical device, infusion needle, or other structure as is understood in the art. The female luer component 70 comprises a distal tubular portion 72 and larger diameter proximal tube 74 provided with one or more external thread segments 76. The external thread segments 76 are sized and configured to threadingly mate with the internal threads 48 of the hub 24.

The proximal tube 74 has an inner lumen 78 which is tapered outwardly in the proximal direction. The taper angle of the wall of lumen 78 preferably approximates the taper angle of the nose 30 of the male luer component 26. Thus, as seen in FIG. 2, the tapered nose 30 fits within the lumen 78 and the hub 24 threadingly engages the exterior thread segments 76 to lock the male and female luer components 26, 70 together in sealing engagement.

Distal axial travel of the hub 24 is limited with respect to the male luer component 26 by the engagement of the tapered shoulder 32 on male luer component 26 and internal annular ramp 50 on hub 24. Thus, the tapered nose 30 and inner lumen 78 are forced into frictional fluid-sealing engagement by rotation of the hub 24 with respect to the male luer component 26. Alternatively, the tapered nose 30 may be engaged with the inner lumen 78 without using the hub 24 by simply advancing the male luer component 26 axially toward the female component 70. A pair of opposed wings 80 or other gripping structures are preferably provided on the female luer component 70 as torque grips for disengaging the male and female luer components, as will be explained more fully below. The female luer component 70 further includes a second lumen 82 within the distal tubular portion 72 and an inner throughhole 84 for providing communication between the first and second lumens 78, 82.

Hub/Male Component Anti-Rotation Structure

In one particular embodiment, the present luer-lock connector can provide for an anti-rotation feature for the hub 24 with respect to the male luer component 26. More specifically, as the hub 24 advances distally over the external thread segments 76, the engagement of the tapered shoulder 32 and internal ramp 50 causes the nose 30 to sealingly engage the first lumen 78. At some point, the engagement between the nose 30 and inner lumen 78 halts further distal movement of the male luer component 26. Further rotation of the hub 24 causes the cooperating ramped surfaces 32, 50 to slide axially relative to each other to produce a relatively tight friction fit between the hub 24 and friction enhancement surface 32.

Figure 8A:
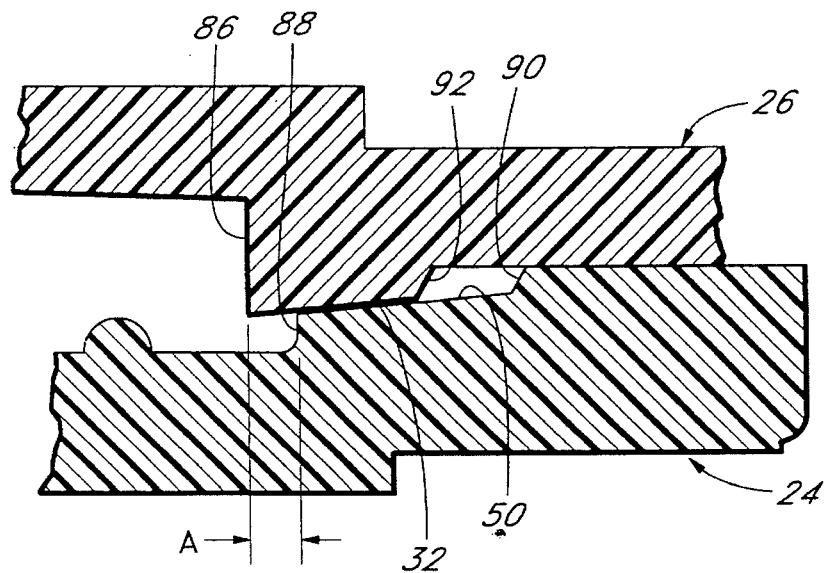
FIGS. 8a–8c show several stages of engagement between friction surfaces of the hub and the male luer component.
Figure 8B:
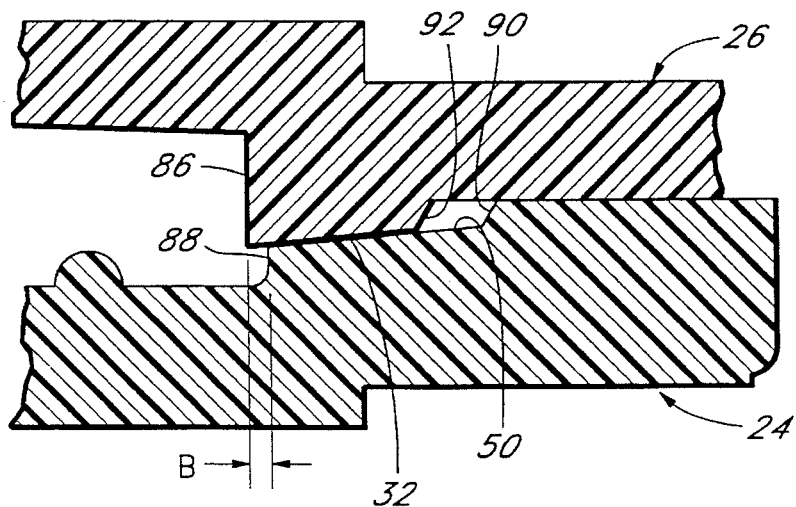
Figure 8C:
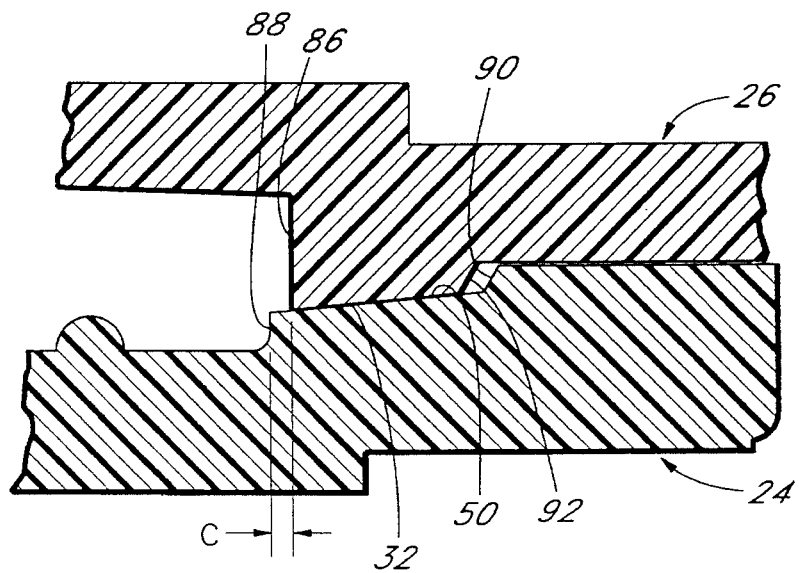

With specific reference to FIGS. 8a–8c, this relative sliding movement is shown. For example, FIG. 8a illustrates a situation when the tapered engagement surfaces 32, 50 are in simple contact without substantial frictional engagement therebetween. This situation might be when the hub 24 has been sufficiently rotated to bring tapered nose 30 into contact with the inner lumen 78. At this point, an exterior step 86 of the male luer component 26 at the distal end of surface 32 is disposed distally by a distance A from an internal step 88 of the hub 24 at the distal end of surface 50.

FIG. 8b illustrates a position wherein the hub 24 has been rotated further over the male luer component 26 causing the frictional engagement surfaces 32, 50 to slide axially relative to one another. At this point, the step 86 is disposed a smaller distance B distally from the step 88 of the hub 24. Finally, in FIG. 8c, the hub 24 has been rotated farther over the exterior thread segment 76 of the female luer component 70 to force the frictional engagement surfaces 32, 50 to slide even more so relative to each other. At this point, the step 86 is disposed proximally to the step 88 by a distance C. Further tightening of the hub 24 will cause a hard stop 90 to contact a proximal stop surface 92 on the male luer component 26.

The stop surfaces 90, 92 may be disposed at approximately 45° angles to the longitudinal axis to prevent further relative axial movement and prevent fracture of either the male luer component 26 or hub 24 from overtightening.

As will be apparent, in all of the axial positions of hub 24 in FIGS. 8a–8c, the hub is frictionally rotationally engaged with the male luer component 26. Thus, the present invention provides an anti-rotation friction throughout an axial range of travel in a manner that minimizes the risk of reverse rotation and loosening of the hub throughout various rotational positions of the hub 24. The relative axial position of the hub 24 with respect to the male luer component 26 is determined by the amount of tightening torque applied thereto, which can differ from operator to operator. The present invention accommodates different application forces by providing an anti-rotation frictional engagement over a range of different tightening torques.

The taper angles of the engagement surfaces 32, 50 are thus selected to provide frictional engagement over a range of axial travel after the point at which the two surfaces initially contact. The shallower the taper angles, the greater the axial travel that can be accomplished between the hub 24 and male luer component 26, within given elastic deformation limits of the hub 24. A relatively steep taper angle, such as is present for engaging thread surfaces, will tend to minimize the axial range of frictional engagement.

In terms of percent of inclination (100% being a 45° taper) the engagement surfaces 32, 50 are preferably identically tapered within the range of from about 1% to about 15% with respect to the longitudinal axis of the tubular bodies. Preferably, the engagement surfaces 32, 50 are typically tapered less than about 10% and within a range of about 2% to about 8%, with a preferred range of between 2% to 6% and an optimum taper of about 5% with respect to the longitudinal axis of the tubular bodies. In one preferred embodiment, with an optimum engagement surface incline of 5%, the axial travel is within the range of from about 0.08 and about 0.18 inches.

Hub/Male Luer Component Rotational Coupling Structure

In accordance with another aspect of the present invention, the present two-piece luer lock connector 20 provides an improved structure for rotationally locking the hub 24 to the male luer component 26. With reference now to FIGS. 2–7, the radially inwardmost edges 53 of the radially inwardly extending ribs 52 on the hub 24 define a circle having approximately the same diameter as the proximal tubular portion 28 of the male luer component 26. The proximal end of the male luer component 26 includes a series of axially extending splines 94 projecting outward from the tubular portion 28. The ribs 52 are dimensioned to interfit in sliding engagement between the splines 94 along guideways 96. Conversely, the splines 94 extend along the channels 54 between the ribs 52. The circumferential dimensions of the ribs 52 and guideways 96 may provide a slight interference tolerance to indicate when the hub 24 and male luer component 26 are rotationally locked.

With specific reference to FIGS. 5 and 6, the male luer component 26 includes at least a central axially elongated spline 94a, preferably also a pair of intermediate splines 94b disposed on either side of the central spline, and most preferably also a third pair of substantially diametrically opposed splines 94c. The distal end of the central spline 94a includes a point 98 leading to a pair of ramped cam surfaces 100. The proximal end of the elongated spline 94a is preferably tapered radially inwardly in the proximal direction and also tapered circumferentially to produce a point 102.

The second and third pairs of splines 94b, 94c form generally rectangular radial projections with the second splines 94b including angled edges 104 facilitating removal of a forming mold. More specifically, the male luer component 26 is preferably formed by two mating semi-cylindrical half-molds with all of the splines 94 being formed by only one of the two molds. In the illustrated embodiment of FIG. 6, the upper mold would form the splines 94 and thus it can be readily seen that the edges 104 allow the mold to be lifted off cleanly.

In a preferred embodiment, there are at least three spline contact points 107 in either rotational sense to provide tangential strength to avoid stripping by the inwardly directed ribs 52, however, the present invention may comprise only one spline 94. Although the preferred embodiment includes splines 94 on only one circumferential half, it should be noted that splines may be formed all the way around the circumference of the male luer component 26 and still achieve many of the inventive aspects herein.

Rotational Coupling Indicator

To provide tactile feedback for an operator when sliding the hub 24 axially in a proximal direction into the rotationally locked position, a circumferentially formed "speed bump" or ridge 106 is provided on the male luer component 26. As seen in FIGS. 5 and 6, the illustrated circumferential ridge 106 is centered at the elongated spline 94a although it can readily be positioned at other locations around the circumference of tubular body 28 or be formed in a 360° circle to act as a retaining ring. The illustrated ridge 106 extends circumferentially in an approximately 90° arc around the tubular portion 28 and has a radially projected height of at least one-half and preferably nearly two-thirds the height of the splines 94. The circumferential ridge 106 is preferably formed with an apex 106a and a pair of ramped surfaces 106b. As the hub 24 is advanced in the proximal direction, the inwardly directed ribs 52 come in contact with the circumferential ridge 106 and the user experiences a more pronounced drag or frictional engagement between the hub 24 and male luer component 26. The size of the ridge 106 and the preferred connector material allow the hub 24 to be advanced across the ridge and flex without damage to either component. In some cases, extreme tolerances may create an additional interference between the inwardly directed ribs 52 and circumferential ridge 106. The ribs 52, being larger, may shave off or deform a small portion of the ridge 106 resulting in a consistent interference and tactile feedback thereafter. The purpose of the ridge 106 is to provide feedback to indicate to an operator when the hub 24 is axially positioned to achieve optimum rotational locking engagement with the male luer component 26.

Figure 12B:
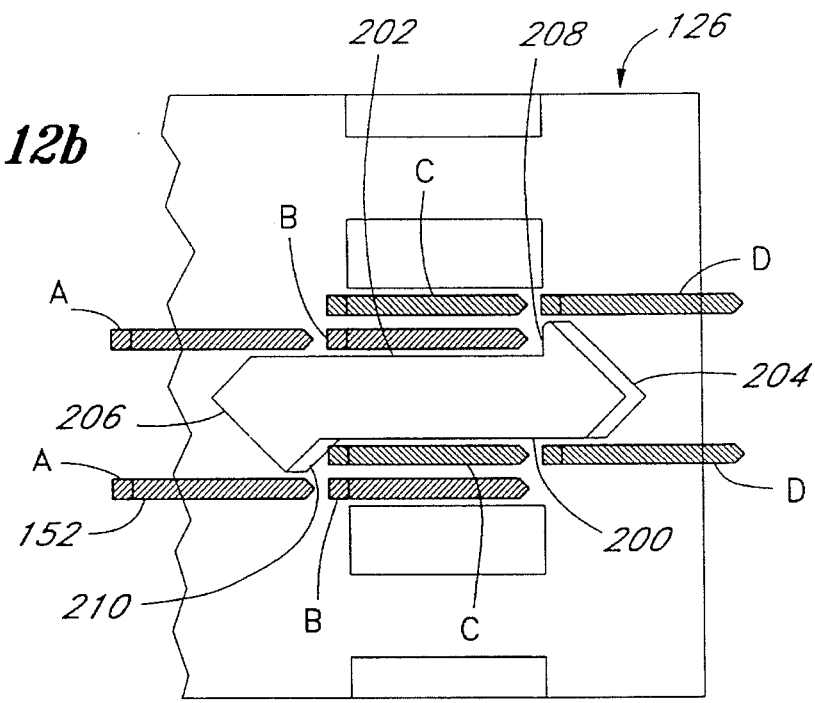
FIG. 12b is a partial plan view of a proximal end of the male luer component showing an alternative spline arrangement and taken along line 12—12 of FIG. 10.

In an alternative embodiment, the diameters of the inwardly directed ribs 52 and proximal tubular portion 28 may be such that there is a net tolerance in the region of the splines 94 to provide this tactile feedback, instead of providing a circumferential ridge 106. Additionally, FIG. 12b illustrates a "keyed" version wherein a stepped spline positively stops the hub in a position coupling the hub and male component. The hub may be removed by rotation with respect to the male component. Other tactile feedback structures for indicating the axial position of the hub 24 can be readily envisioned by one of skill in the art in view of the disclosure herein.

Hub Removal

As there is no travel limiting structure in the proximal direction from the splines 94 and ridge 106, the hub 24 can be completely removed from the proximal end of the male luer component 26. The hub 24 can thus be slid proximally along a supply line (not shown) to remove it from the immediate connector site. This may be advantageous in neo-natal, pediatric or other applications where the relatively large diameter of the hub 24 is an impediment to proper positioning of the connector and associated medical components, and may cause a pressure point on the skin.

Hub/Male Component Rotational Registry

The cam surfaces 100 on the distal end of the elongated central spline 94a ensure the proper rotational registry of the hub 24 with the splines 94. The proximal ends of the ribs 52 are tapered at 108 to form guide points. As the hub 24 is slid proximally along the male luer component 26, the distal point 98 on the central spline 94a will initially contact the inwardly directed ribs 52. The ribs 52 may either be aligned with the channels 96 or with the central elongated spline 94a. In the latter case, the guide points 108 will contact one or the other of the cam surfaces 100 on either side of the proximal point 98, and the hub 24 will be caused to rotate into proper rib/spline alignment.

Similarly, distal travel of the hub 24 onto the male component 26 may initially bring point 102 into contact with a corresponding point on the distal end of one of the ribs 52. Further distal advancement of the hub 24 will cause an appropriate rotational alignment of the ribs 52 with channels 96.

Specific Embodiment

A particular embodiment of the present two-piece luer connector 20 will now be described. The particular dimensions can be modified to suit the needs of any particular use environment, as will be understood by one of skill in the art. In this particular embodiment, the male component 26 has an overall length of about 1.12 inches, with an outside diameter of the proximal tubular portion 28 being approximately 0.236 inches. The step 86 on the tapered shoulder begins at approximately 0.435 inches from the distal tip of the tubular body 26 and the tapered surface 32 has an axial length of approximately 0.065 inches. The small diameter on the proximal end of the tapered step 32 is approximately 0.269 inches, while the large diameter is approximately 0.275 inches of the hub 24.

In one embodiment, hub 24 has an overall length of approximately 0.54 inches, and the inwardly directed ribs 52 define a cylinder having a diameter of approximately 0.240 inches, resulting in a about 0.004-inch nominal clearance between the ribs and the proximal tubular portion 28. The annular inclined surface 50 on the hub 24 preferably has an axial length of approximately 0.088 inches, a small diameter of approximately 0.266 inches, and a large diameter of approximately 0.279 inches.

The ribs 52 may have an axial length of approximately 0.127 inches, while the axial length of the intermediate and diametrically opposed splines 94b, 94c have an axial length of about 0.123 inches. The central spline 94a has an axial length from distal point 98 to proximal point 102 of approximately 0.223 inches. The circumferential ridge 106 preferably extends 90° around the male tubular portion 28 and has a radial height of approximately 0.008 inches at its apex 106a. The hub 24 has a preferred nominal wall thickness of approximately 0.039 inches, while the male luer component 26 has a minimum wall thickness in the proximal tubular portion 28 of approximately 0.047 inches.

Materials

The components of the two-piece luer connector 20 are preferably injection molded using known biocompatible materials. More specifically, the materials are preferably resistant to corrosion from chemicals, such as alcohol and/or lipids, common in medical environments. For example, ABS (available from BASF under the trade name TERLUX™) may be used for the hub 24 and acrylic, polycarbonate or other material for the male and female components 26, 70. Polypropylene is used for the protector cap 22 to allow for deformation from the tolerance interference with the male luer component 26 during assembly and to enhance resistance therebetween, preventing the cap from falling off. The materials used for the male component 26 and hub 24 are preferably dissimilar to enhance the frictional engagement between the surfaces 32, 50.

Alternative Anti-Rotation Structure

In an alternative embodiment to the frictional engagement between the surfaces 32, 50, the hub 24 and male luer component 26 may be provided with a ratchet-type engagement. In this embodiment, either the hub 24 or male luer component 26 is provided with one or more detents, which engage grooves in the opposite component to securely lock the hub relative to the male luer component. Such a ratchet configuration is shown and described with reference to FIGS. 19 and 20. Other types of complementary surface structures can be readily provided which, through elastic deformation during tightening, provide a relatively high resistance to reverse hub rotation.

Operation of Luer-Lock Connector of FIGS. 1–8

In operation, the nose 30 of the male luer component 26 is inserted within the tapered lumen of the female luer component 70. The hub 24 is advanced in a distal direction so as to engage the inwardly extending threads 48 with the external thread segments 76. The hub 24 is then rotated relative to both the male and female components 26, 70 to advance over the external thread segments 76 without applying a torque to any hoses connected to the male and female components. At some point, the tapered nose 30 will be forced into sealing engagement with the lumen 78 and the male luer component 26 will experience resistance to further advancement into the female luer component 70. Depending on the tightening torque applied by the user, the hub 24 may be advanced a short distance further causing the tapered engagement surfaces 32, 50 to slide relative to each other, as previously described. Thus, the male and female luer connectors 26, 70 are firmly attached, and the hub 24 is frictionally rotationally engaged on the tapered annular shoulder 32. To remove the hub 24, the operator grasps the wings 80 or other structure of the female luer component 70 and rotates the hub to disengage the engagement surfaces 32, 50 and reverse the internal threads 48 from the external thread segments 76.

The amount of torque required to remove the hub 24 is sufficient to minimize the risk of inadvertent hub rotation, and may in some embodiments be even slightly greater than the torque applied in tightening. This is due to the greater coefficient of static friction between the tapered engaging surfaces 32, 50 achieved by the present invention than their relative coefficient of sliding friction.

To illustrate this point, tests were made on various prior art luer connectors to determine the amount of torque required to untwist a sleeve or hub after tightening a predetermined amount. During the test procedure, all of the fittings were dry and tightened to a torque of 16 in-oz. The connector components embodying the present invention were injection molded from K resin from Phillips for the hub 24, and G-20 Hiflow acrylic from Cyro Industries for the male and female components 26, 70. The specific materials may be otherwise, but are preferably resistant to corrosion from chemicals, such as alcohol and/or lipids, common in medical environments. The surface 32 and surface 50 were each inclined at an angle of 5° from the longitudinal axis of the connector. Five different trials were staged to determine the torque required to disassemble the hubs from the various fittings. Finally, an average of the five trials is given. The results appear below in Table 1.

TABLE 1

| Comparative Disassembly Torques for Luer Hubs (in.-oz.) | | | | | | |
|---|---|---|---|---|---|---|
| Company | | | | | | |
| Abbott | Abbott | Baxter (new) | Baxter (old) | Borla | IVAC | t Siemens n)d |
| 13 | 10 | 5.5 | 5.5 | 8 | 9.5 | 65 |
| 11 | 9.5 | 5 | 5.5 | 8.5 | 10 | 5.5 |
| 11 | 9.5 | 5.5 | 5.5 | 9 | 11.5 | 4.5 |
| 11 | 9 | 5.5 | 4.5 | 8 | 11 | 7 |
| 10.5 | 7 | 5.5 | 5.5 | 8 | 20 | 6.55 |
| | | | | | | 5 |
| Total 56.5 | 45 | 27 | 26.5 | 41.5 | 62 | 29.58 |
| Average 11.3 | 9 | 5.4 | 5.3 | 8.3 | 12.4 | 5.98 |

After untightening of the hub 24 from the surface 32 of the male luer component 26, the hub is in a position enabling it to be freely rotated with respect to the male luer component. Although not shown, this position is somewhere between the illustrations of FIGS. 2 and 3, with the ribs 52 between the tapered shoulder 32 and the splines 94. In a more proximal position of the hub 24, the axial ribs 52 are in registry with the splines 94 to rotationally lock the hub 24 with respect to the male luer component 26. The larger diameter hub 24 increases the torque available to unlock the male luer component 26 from frictional engagement with the female luer component 70. This is shown in FIG. 3. Finally, as described above, the hub 24 may be retracted in a proximal direction completely from the male luer component 26 in a still further position along the fluid conduit.

Alternative Protective Cap

Figure 9:
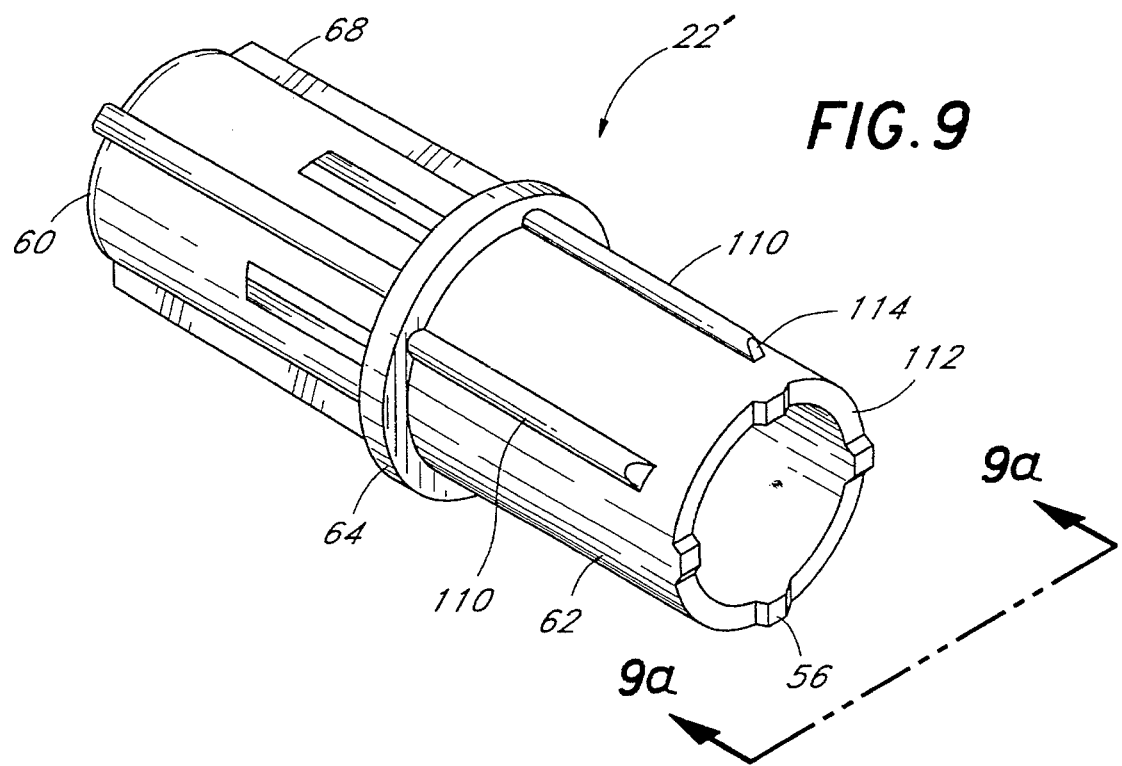
FIG. 9 is a perspective view of a preferred protector cap for the two-piece luer-lock connector.
Figure 9A:
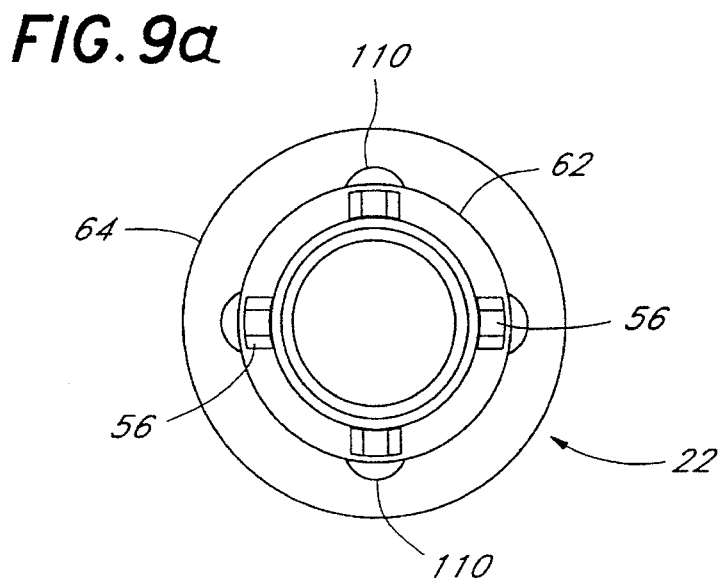
FIG. 9a is an elevational view of an end of the protector cap taken along line 9a—9a of FIG. 9.

The protective cap 22 previously disclosed for mating with the male luer component 26 included a smooth outer engagement surface 62. FIGS. 9 and 9a illustrate an alternative protective cap 22' which includes a series of outwardly directed ribs 110 on the cylindrical engagement portion 62. The ribs 110 are provided to engage the inwardly directed threads on the hub of the present luer connector. This engagement is illustrated in FIG. 10, as will be described below. The ribs 110 extend from the annular flange 64 toward a proximal open end 112 and terminate at ramped surfaces 114. The ribs 110 are preferably rounded in cross-section. It has been recognized that the material of the protector cap 22', preferably polyethylene, shrinks during exposure to the sterilization environment. In contrast, the materials of the male luer connector and hub are less susceptible to dimensional changes during sterilization. Thus, an interference fit provided between a smooth engagement portion 62 and inwardly directed threads 48 prior to sterilization leads to a relatively loose fit after sterilization. Unfortunately, attempts to solve this problem by increasing the diameter of the tubular portion 62 prevents initial engagement between the protective cap 22 and hub 24. Thus, the present invention contemplates providing the axially directed ribs 110 to allow for an increased initial interference fit between the ribs and the inwardly directed threads of the hub. After sterilization, the protective cap 22' has undergone some shrinkage, but the ribs 110 still provide a sufficient frictional engagement with the inwardly directed threads of the hub to retain the protective cap over the nose of the male luer component.

Alternative Luer-Lock Connector

FIG. 10 is a cross-sectional view showing an alternative two-piece medical luer lock connector 120 engaged by the aforementioned protector cap 22'. The two-piece luer lock connector 120 comprises a hub 124 and a tubular male luer component 126. The male luer component 126 comprises an elongate tubular body having a proximal tubular section 128, a tapered nose 130, and a tapered shoulder 132 disposed therebetween. A central lumen consists of a distal conduit 134, a larger proximal conduit 136, and a step 138 disposed therebetween. The proximal conduit 136 terminates in a flared mouth 140 for receiving a flexible delivery hose (not shown) which may be inserted all the way to the step 138 and glued or otherwise adhered into place.

The hub 124 comprises a generally tubular sleeve having a proximal cylindrical surface 142, a distal annular flange 144, and a series of axially extending short and long grip rails 146a, 146b. The hub 124 includes three distinct interior surface regions. The first distal interior region has single or multiple internal threads 148. The internal threads 148 are preferably standard ISO threads. A proximal end of the distal interior region terminates at an anti-rotational friction enhancing structure such as an annular internal taper 150. Finally, a proximal interior region of the hub 124 includes a plurality of radially inwardly directed ribs 152 separated by channels 154 (see FIG. 13). The functions of the internal surfaces of the hub 124 will be described more fully below.

As mentioned previously, the two-piece luer-lock connector 120 is provided prior to use with the protective cap 22'. As seen in FIG. 10, the outwardly directed ribs 110 on the protective cap 22' engage with the inwardly directed threads 148 on the hub 124. The slight interference provides a gripping force thus preventing the protective cap 22 from sliding from within the hub 124. The present invention has been designed to provide a consistent grip between the protective cap 22' and hub 124. More particularly, the threads 148 have a predetermined pitch, and the ribs 110 a predetermined length, so that each rib contacts two of the threads at all times. This results in a eight points of contact between the protective cap 22' and the hub 124 in any rotational orientation therebetween. Thus, even with slight variations in tolerances, there will always be eight points of contact resulting a fairly consistent frictional engagement. In the alternative, an outer cylindrical step 156 on the tubular nose 130 frictionally engages an inner diameter of an alternative protective cap (not shown). This frictional engagement is utilized when the hub 124 is not present.

The two-piece luer-lock connector 120 is adapted to couple to a second tubular body, such as the female luer component 70 shown in FIG. 2. As described previously, the protective cap 22' is removed and the nose 130 of the male luer component 126 inserted within a similarly tapered proximal tube on the female luer component. The hub 124 may be used to axially engage the male luer component 126 with the female luer component. With reference to FIG. 11, the inwardly directed ribs 152 have angled distal surfaces 158 which engage with angled steps 160 on the exterior of the male luer component 126, disposed distally from the tapered shoulder 132. Engagement between the angled surfaces 158 and 160 prevent the hub 124 from sliding in a distal direction relative to the male luer component 126. Thus, the hub is used to displace the male luer component 126 toward the female luer component. In this manner, the tapered nose 130 is engaged within the internal taper of the female luer component. The hub 124 may be utilized to lock the two components together, or may be removed.

As mentioned previously, the female luer component is provided with one or more external thread segments, such as those shown at 76 in FIG. 2. The thread segments are sized and configured to mate with the internal threads 148 of the hub 124. The hub 124 rotates freely over the coupled male and female luer components to advance the internal threads 148 over the external threads of the female luer component. Eventually, the angled distal surfaces of the ribs 152 contacts the angled step 160 on the exterior of the male luer component 126. At this point, the nose 130 is forced into the tapered inner tubular portion of the female luer component. When the nose 130 fits tightly within the tapered lumen of the female luer component, the frictional engagement between the angled surfaces 158, 160 provides a slight antirotation feature for the hub 124 with respect to the male luer component 126. More specifically, the surfaces 158, 160 are preferably angled within the range of about 30° to 60°, and preferably approximately 45°, and undergo a small frictional engagement upon tightening of the hub 124. This minimal frictional engagement helps prevent the hub 124 from coming loose.

The male luer component 126 is also provided with the tapered shoulder 132 at a relatively shallow angle with respect to a central axis to couple with the first-described hub 24. The angle of the tapered shoulder 132 is preferably within the range of 0.5° to 7°. As mentioned previously with respect to the engaging tapered surfaces 32, 50 of the embodiment of FIGS. 1–8, the male luer component 126 is adapted to receive the hub 24. More particularly, the inner frictional engagement surface 50 of the hub 24 is sized to engage the outer tapered shoulder 132 of the male luer component 126. Thus, the aforementioned frictional engagement having a range of axial travel of the hub 24 over the male luer component 126 is provided.

Figure 13:
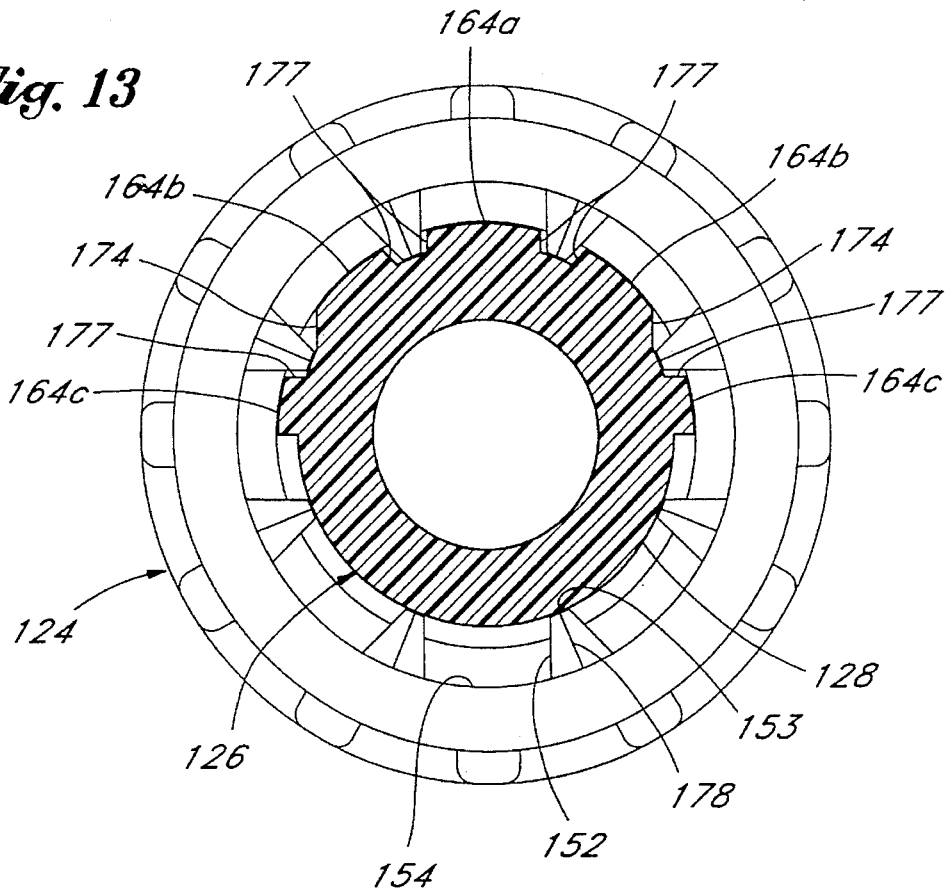
FIG. 13 is a cross-sectional view of the interaction between the proximal end of the male luer component and the rotatable hub of FIG. 10.

As in the previous embodiment, the two-piece luer lock connector 120 includes structure for rotationally locking the hub 124 to the male luer component 126. With reference to FIGS. 12*a*, 12*b*, and 13, the radially inner edges 153 of the ribs 152 define a circle have approximately the same diameter as the proximal tubular portion 128 of the male luer component 126. The proximal end of the male luer component 126 includes a series of axially extending splines 164 projecting outward from the tubular portion 128. The ribs 152 are dimensioned to interfit in sliding engagement between the splines 164 along guideways 166. Conversely, the splines 164 extend along the channels 154 between the ribs 152. Alternatively, the circumferential dimensions of the ribs 152 and guideways 166 may provide a slight interference tolerance to indicate when the hub 124 and male luer component 126 are rotationally coupled. In the preferred embodiment, a separate circumferential ridge, or "speed bump," as described below, is provided.

With reference to FIG. 12*a*, the male luer component 126 includes at least a central axially elongate spline 164*a* along its exterior surface, and preferably also includes a first pair of intermediate splines 164*b* disposed on either side of the central spline. Furthermore, a second pair of substantially diametrically opposed splines 164*c* is also provided. The distal end of the central spline 164*a* terminates in a point 168 between a pair of ramped cam surfaces 170. The proximal end of the elongate spline 164*a* is preferably tapered radially inwardly in the proximal direction, and also tapered circumferentially to result in a pointed ramp 172.

The first and second pairs of splines 164*b* and 164*c* form generally rectangular radial projections with the intermediate splines 164*b* including angled edges 174 facilitating removal of a forming mold. More specifically, the male luer component 126 is preferably formed by two mating semi-cylindrical half-molds with all of the splines 164 being formed by only one of the two molds. In the embodiment of FIG. 12*a*, the upper mold would form the ridges 164 and it can be readily seen that the edges 174 allow the mold to be lifted off cleanly. This arrangement increases the potential mold cavity density in the manufacturing molds. Specifically, the elimination of certain slides used to form undercuts allows the mold cavity density to increase from 32 or 48 cavities per mold to 64 cavities per mold. Each cavity forms an individual part in each mold. It will be readily apparent to one of skill in the art that the increased mold cavity density by a factor of two greatly speeds the manufacturing process, and reduces the expense associated with manufacturing the molds.

In the preferred embodiment, there are at least three spline contact points 177 in either rotational sense to provide tangential strength to avoid stripping the splines 164 by the inwardly directed ribs 152. However, the present invention may comprise only one spline 164. Also, although the preferred embodiment includes splines 164 on only one circumferential half, it should be noted that splines may be formed all the way around the circumference of the male luer component 126 and still exhibit many of the inventive aspects herein.

Tactile feedback for an operator when sliding the hub 124 axially in a proximal direction into the rotationally locked position is provided by a circumferentially formed ridge 176 on the male luer component 126. As seen in FIG. 12a, the circumferential ridge 176 is centered at the elongated spline 164a, although it can be readily positioned at other locations around the circumference of the tubular body 128, or be formed in a 360° circle to act as a retaining ring. The illustrated ridge 176 extends circumferentially in an approximately 90° arc around the tubular portion 128 and has a radially projected height of at least one half and preferably approximately two-thirds the height of the splines 164. In contrast to the previously described circumferential ridge 106 shown in FIG. 5, the circumferential ridge 176 seen in FIG. 12a is formed with a flat apex 176a and a pair of outer ramped surfaces 176b. As the hub 124 advances in the proximal direction, the inwardly directed ribs 152 come into contact with the circumferential ridge 176 and the user experiences a more pronounced drag or frictional engagement between the hub 124 and male luer component 126 due to the increased surface area contact therebetween. The height of the ridge 176 and the preferred connector material allow the hub 124 to advance across the ridge and flex without damage to either component. The ribs 152 may shave off or deform a small portion of the ridge 176, in cases of extreme tolerance interference, resulting in a consistent tactile feedback thereafter. The ridge 176 provides tactile feedback to an operator to indicate when the hub 124 is axially positioned to achieve optimum rotational locking engagement with the male luer component 126. As mentioned previously, other tactile feedback structure to indicate this preferred axial position of the hub 124 over the male luer component 126 is contemplated.

In a comparison of FIGS. 7 and 13, the ribs 152 are narrower than the previously described ribs 52. The radially inward points 153 in contact with the male luer component 126 are thus narrower. The narrower ribs 152 facilitate automated assembly of the hub 124 onto the male luer component 126. It has been discovered through empirical tests that the narrower ribs 152 allow for some rotational movement between the hub 124 and the male luer component 126. Because of this rotational looseness, the ribs 152 may not travel over the same circumferential location of the circumferential ridge 176 every time the hub 124 is reversed proximally over the male luer component 126. This led to some inconsistency in the tactile feedback the operator experiences when attempting to locate the hub 124 in a rotationally locked position with respect to the male luer component 126. To solve this problem, the splines 164a, b, c have been widened in the circumferential direction to provide narrower guideways 166. In one particular embodiment, the tubular portion 128 has a diameter of approximately 0.236 inches, the central spline 164a has a circumferential width of approximately 0.070 inches, the splines 164b have an effective circumferential width of approximately 0.035 inches, while the tapered ribs 152 are spaced apart 0.080 inches at their bases. The wider splines 164 cause the ribs 152 to travel across the same location on the circumferential ridge 176 every time the hub 124 is displaced into rotational engagement with the male luer component 126. Furthermore, the flat 176a formed on the apex of the ridge 176 reduces wear of the ridge thus further ensuring a consistent tactile feedback for the operator.

As there is no travel limiting structure in the proximal direction from the splines 164 and ridge 176, the hub 124 can be completely removed from the proximal end of the male luer component 126. As described previously, the hub 124 can be slid proximally along a supply line (not shown) to remove it from the immediate connector site.

The cam surfaces 170 on the distal end of the elongate central spline 164a ensure the proper rotational registry of the hub 124 with the splines 164. The proximal end of the ribs 152 are tapered at 178 to form guide points. As the hub 124 is slide proximally along the male luer component 126, the distal point 168 on the central spline 164a will initially contact the inwardly directed rib 152. The ribs 152 may either be aligned with the channels 166 or with the central elongate spline 164a. In the latter case, the guide points 178 will contact one or the other of the cam surfaces 170 on either side of the proximal point 168, and the hub 124 will be caused to rotate into proper rib/spline alignment. Similarly, distal travel of the hub 124 onto the male component 126 may initially bring point 172 into contact with the distal end of one of the ribs 152. Further distal advancement of the hub 124 will cause an appropriate rotational alignment of the ribs 152 into channel 166.

Alternative "Keyed" Rotational Coupling Indicator

In an alternative embodiment, a positive stop may be provided to temporarily prevent the hub 124 from being removed in a proximal direction from the male luer component 126. Referring to FIG. 12b, a central "keyed" spline 200 may be provided in place of either the spline 94a or 164a. The spline 200 is defined by a central constant width portion 202, a proximal arrowhead portion 204, and a distal arrowhead portion 206. Projections of pairs of adjacent ribs 152 are illustrated in FIG. 12b. That is, the radially inward surfaces 153 of the ribs 152 are projected on the male luer component 126. Thus, in a first position A, the ribs 152 are disposed proximate the distal arrowhead portion 206. The spacing between the ribs 152 is slightly greater than the circumferential width of the distal arrowhead portion 206. The arrowhead portion 206 is provided with an apex and a pair of adjacent cam surfaces to guide the ribs 152 therearound.

In a second position B the ribs have advanced proximally to lie adjacent the central constant width portion 202 and within the guideways 166. A proximal end of one of the ribs is prevented from further proximal movement by a stop surface 208 formed on the proximal arrowhead portion 204. Further proximal movement of the hub 124 is prevented. To remove the hub 124 from the male luer component 126, the hub is rotated, as with turning a key, to place the ribs 152 in the position C. From the position C, the hub may be translated proximally so that the ribs are in the position D, and the hub may be removed completely. In the position D, it can be seen that the proximal arrowhead portion 204 is sized slightly smaller than the spacing between the ribs 152. In the reverse sequence, the ribs are guided around the proximal arrowhead portion 204 by its taper, and then automatically around the distal arrowhead portion 206 by virtue of an angled surface 210 provided thereon. The stop surface 208 provides a positive tactile feedback indicating to the operator that the hub 124 is in an axial position in which it is rotationally locked with respect to the male luer component 126.

The embodiment shown in FIG. 12b eliminates the need for a circumferential "speed bump," but it will be appreciated that one may be provided for redundancy. For example, one or more small bumps 211 are preferably formed on the exterior of the male luer component 126 between at least two of the splines, in this case shown between the central constant width portion 202 of the spline 200 and the adjacent intermediate splines. The ribs 152 interfere with these bumps 211 so that the hub 124 must be forced thereover when rotated before being displaced proximally from the male component 126. This provides tactile feedback to the user indicating the rotational position of the hub 124.

Hub/Male Luer Component Snap Ring

In a further aspect of the present invention, a circumferential ridge or other such structure may be provided on the male luer component 126 to allow the hub 124 to be advanced distally thereon, but prevent the hub from being removed proximally. As seen in FIGS. 14a and 14b, a circumferential retaining ring 220 is illustrated projecting from the tubular portion 128 of the male luer component 126. The hub 124 advances in a distal direction as seen by the arrows 222. Diametrically opposed axial slits 224 provided in the proximal end of the male luer component 126 allow a slight inward flexing at that location when the ribs 152 cam over the retaining ring 220. In other words, the ribs 152 define a circle having approximately the same diameter as the tubular portion 128. Thus, the interference with the retaining ring 220 causes the proximal end of the male luer component 126 to be compressed inward by virtue of the slits 224. FIG. 14b illustrates the hub 124 after having been "snapped" over the retaining ring 220 and advanced distally onto the male luer component 126. The proximal end of the male luer component 126 has resiliently recovered into its original position. Reversing the direction of the hub 124 in a proximal direction over the male luer component 126 causes a rear edge 226 to come into contact with the retaining ring 220. Because there is no ramp surface on the proximal end of the ribs 152, the hub 124 is retained on the male luer component 126. In the presently illustrated form, the retaining ring 220 is rounded or angled and the hub 142 can be removed from the proximal end of the male luer component 124 with the application of sufficient force. However, other embodiments rigidly preventing removal of the hub 124 in this manner are contemplated.

Female Luer Component Breather Cap

FIGS. 15 and 15a illustrate a preferred protective cap 230 for the female luer component 70 described with reference to FIGS. 1–8. As mentioned, the female luer component 70 is provided with external threads 76. The protective cap 230 includes inner threads 232 sized and shaped to mate with the threads 76. Preferably, the cap 230 includes dual threads 232a and 232b. The cap 230 is advanced over the female luer component 70 until a distal end 234 of the female component contacts a plurality of radially oriented bumpers 236 provided on the interior of a closed end 238 of the cap 230. The bumpers 236 function in a similar manner as the projections 56 on the end of the protective cap 22 for the male luer component. In other words, the bumpers 236 provide a small gap between the protective cap 230 and the female luer component 70 to facilitate sterilization while the cap is in place. The female luer component 70 can thus "breathe" with the cap 230 installed while providing a tortuous path to prevent contamination of the fluid pathway. In the alternative, the bumpers 236 may be eliminated for a "non-breather" type of cap 230. In this embodiment, the proximal end of the female luer component 70 forms a seal with the interior of the closed end 238 of the cap 230.

The cap 230 also incorporates dual helical "crush threads" 240a, 240b formed adjacent the threads 232a, b. The crush threads 240a, b extend radially inward to interfere with the major diameter of the female luer component threads 76. The interference creates a frictional fit between the cap 230 and female luer component 70 preventing inadvertent decoupling. In one embodiment, the major diameter of the female luer component threads 76 is approximately 0.306 inches, while the inner diameter of the crush threads 240a, b is approximately 0.300 inches, resulting in an interference of 0.006 inches. This will yield a frictional torque resisting decoupling of the cap 230 of approximately 70.0 oz-in. The crush threads 240a, b are only formed on the last half-turn of the inner threads 232a, b with sufficient length to run past the major diameter of the female thread 76 to prevent compression and a possible set from occuring during sterilization. The crush threads 240a, b are desirably disposed approximately 180° apart to prevent "cocking" of the protective cap 230 when threaded over the female luer component 70. Previous attempts at creating an interference between a protective cap and female component consisted of sizing the inner thread diameter smaller. Since the cap is often hard to assemble on the end of the female component due to tolerance extremes, fatigue of the assembler may result. The embodiment illustrated in FIGS. 15 and 15a allows the threads on the cap 230 to be sized to fit easily over the female component even after shrinkage, and the crush threads 240 provide an interference during the latter part of the assembly.

Other variations of the crush threads 240a, b are contemplated. For example, the threads 232a, b may be dimensionally altered or may have a varying pitch toward the closed end 238 of the cap 230. The threads 240a, b may also be replaced with discrete bumps or other protrusions which interfere with the female threads 76. In all of these variations, the frictional interference is maintained after sterilization and only comes into effect after the cap 230 has been substantially threaded onto the female component 70.

The material of the cap 230 is soft enough to allow deformation of the crush threads 240a, b, but will not deform the exterior threads 76 of the female luer component 70. The material of the cap 230 is preferably polyethylene, while the female luer component 70 is acrylic, or other alcohol and/or lipid resistant material.

One-Piece Hub/Male Luer Component

Figure 16:
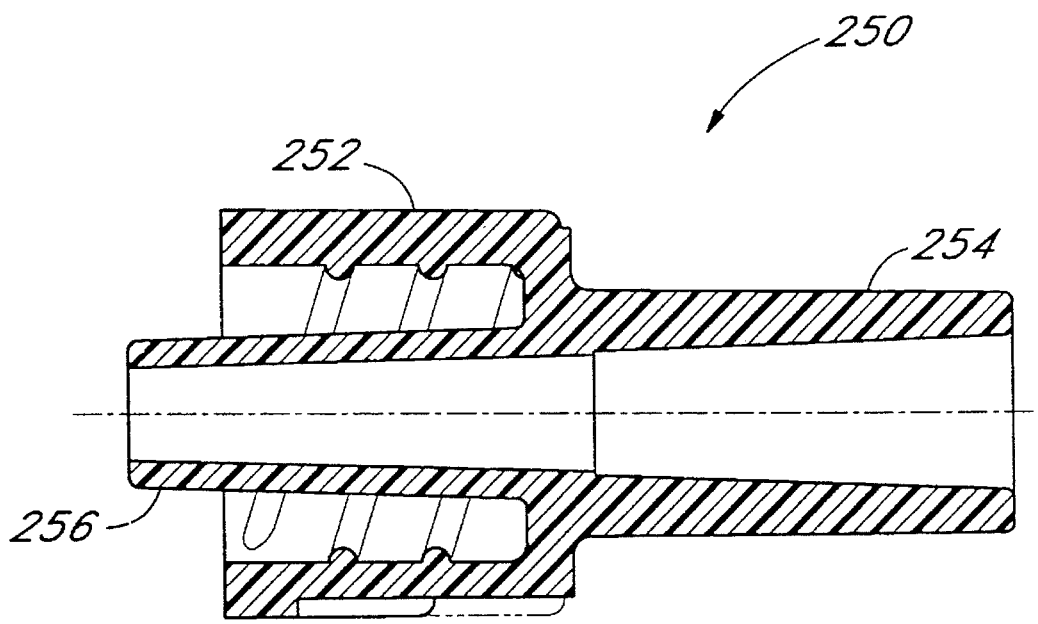
FIG. 16 is a cross-sectional view of a one-piece male luer component and hub.

FIG. 16 illustrates a one-piece hub/male luer component 250. In this embodiment, a hub portion 252 is formed integrally with a male luer portion 254. Although some versatility is lost because the hub portion 252 no longer spins freely with respect to the male luer portion 254, the one-piece component 250 is often desirable. In particular, in small tubing (conduit) applications. The one-piece component 250 facilitates axial engagement of the tapered nose 256 with the inner taper on a female luer component. If desired, the inner threads on the hub portion 252 can engage the threads on the female luer component to lock the connector together.

Hex Anti-Rotation Coupling

Another type of anti-rotation structure between a male luer component 260 and an outer hub 262 is seen in FIGS. 17 and 18. The male component 260 comprises a distal nose portion 264, a proximal hose-receiving tube 266, and a cylindrical flange 268 therebetween. An inner lumen is defined by three passages increasing in size from the distal end to proximal end. More particularly, the lumen includes a distal first passage 270a, and second passage 270b, and a third passage 270c. Two transition regions 272a, 272b provided hose stops between the first and second passages 270a, b and between the second and third passages 270b, c, respectively.

The hub 262 has a generally cylindrical sleeve portion 274 with a circular lip 276 extending radially inward at a proximal end. The lip 276 includes a polygonal inner edge 278, preferably formed as a dodecahedron with 12 sides, which mates with a polygonal exterior portion 280, preferably formed as a hexagon, on the male component 260 adjacent to the flange 268 in the proximal direction. The polygonal inner edge 278 includes parallel sides spaced apart a distance less than the outer diameter of the flange 268. Thus, the hub 262 is prevented from axial travel along the male component 260 by virtue of the interference between the inner edge 278 and flange 268. The hub 262 can thus be used to axially displace the male component 260 into engagement with a female component (not shown) to form a luer connection. To assist in engaging or disengaging the luer connection, the hub 262 rotationally couples with the male component 260 at the polygonal inner edge 278 and polygonal exterior portion 280. Thus, tight fits between the nose portion 264 and tapered lumen of the female component may be broken more easily by rotating the hub 262 with respect to the wings of the female component.

Ratchet-Type Hub/Male Component Coupling

FIGS. 19 and 20 illustrate a coupling between a hub 290 and a male luer component 292 which prevents relative rotation in one direction yet allows limited relative rotation in the other direction. More specifically, the hub 290 may advance the male luer component 292 onto a female luer component, whereupon the hub can rotate freely relative to the male component without causing the male luer to twist.

The male component 292 comprises a tubular hose-receiving portion 294 having exterior ratchet splines 296 thereon, a tapered shoulder 298 and a distal nose 300. A central stepped lumen 302 extends through the male component 292. The hub 290 is defined by a sleeve-like portion 304 having internal threads 306, a proximal region 308 having a plurality of cantilevered fingers 310 separated by axial gaps 312, and a transition region 313 with an internal taper 314. The fingers 310 are distributed around and extend proximally from the transition region 313 to form a plurality of curved cantilevered beams surrounding the tubular portion 294 of the male component 292.

As seen in FIG. 20, the inner surface of each finger 310 defines at least two and preferably three axially aligned teeth 316 sized and shaped to mate with the splines 296. The teeth 316 and splines are so configured to allow the fingers 310 to cam over the splines when the hub 290 rotates with respect to the male component 292 in a clockwise direction as viewed from the perspective of FIG. 20. This rotation corresponds to the direction for advancing the threads 306 onto the female component. The resiliency of the fingers 310 is great enough to withstand relative hub/male component rotation, however, below a certain relative torque threshold.

The male component 292 is rotated along with the hub 292 as the hub advances on the female component by virtue of the interference between the tapered shoulder 298 and internal taper 314 until the nose 300 is firmly lodged in a tapered lumen. At this point, the hub 290 "skips" over the male component and the teeth 316 make an audible clicking sound as they cam over the splines 296. In this manner, twisting of the luer connection is prevented during assembly of a male component to a female component. Overtightening is prevented by the interference between the 45° of the tapered shoulder 298 and internal taper 314. Reverse rotation of the hub 290 with respect to the male component 292 is prevented by the specific shape of the spline/teeth interface, so that the luer connection remains secure despite vibration or inadvertent jostling. The luer connection is broken by forced rotation of the hub 290 in a counter-clockwise direction while holding firm the female component wings.

Although the present invention has been described in terms of certain preferred embodiments, other embodiments can be readily devised by one of skill in the art in view of the foregoing, which will also use the basic concepts of the present invention. Accordingly, the scope of the present invention is to be defined by reference to the attached claims.

What is claimed is:

1. A medical connector, comprising:
   an elongate tubular body having a proximal and a distal end, and a central lumen extending axially therethrough;
   a hub on the tubular body, movable between a distal position in which the hub is rotatable about the tubular body, and a proximal position in which the hub is rotationally locked with respect to the tubular body;
   a first friction engagement surface on the tubular body;
   a complementary second friction engagement surface on the hub; and
   at least one ridge on the tubular body for indicating when the hub is in the proximal position and rotationally locked to the tubular body,
   wherein said first and second engagement surfaces contact each other when the hub is in the distal position and cooperate to resist rotation of the hub with respect to the tubular body.

2. A connector as in claim 1, wherein said tubular body further comprises at least one radially outwardly extending projection for rotationally locking the hub when the hub is in the proximal position.

3. A connector as in claim 2, wherein said hub further comprises at least one axially extending channel on the radially interior surface thereof, for receiving said projection, such that the hub is rotationally locked with respect to the tubular body when the projection is positioned within the channel, and wherein the hub remains axially movable with respect to the tubular body.

4. A connector as in claim 3, wherein said projection comprises an axially extending spline.

5. A connector as in claim 4, wherein said spline tapers axially in the distal direction to provide a distally directed point.

6. A connector as in claim 1, wherein said first friction engagement surface comprises an annular surface surrounding said tubular body, said surface inclined radially outwardly in the distal direction.

7. A connector as in claim 6, wherein said first friction engagement surface inclines within the range of from about 1% to about 15% with respect to the longitudinal axis of the tubular body.

8. A connector as in claim 7, wherein said first friction engagement surface inclines within the range of from about 3% to about 8% with respect to the longitudinal axis of the tubular body.

9. A connector as in claim 6, wherein said second friction engagement surface comprises an annular surface on the radially interior wall of the hub, said annular surface inclined radially outwardly in the distal direction.

10. A connector as in claim 9, wherein each of said first and said second friction engagement surfaces incline radially outwardly in the distal direction at an angle of about 5% with respect to the longitudinal axis of the tubular body.

11. A connector as in claim 1, wherein said tubular body further includes at least one radially outwardly extending projection, which comprises an axially extending spline, and wherein said spline comprises a plurality of wide portions extending in opposite circumferential directions.

12. A connector as in claim 1, wherein said tubular body further comprises a distal tapered nose, and wherein said connector further comprises a cap adapted for fitting over and protecting said nose, said cap including a plurality of projections which are adapted for forming a gap between the cap and the tubular body when the cap is placed over the tapered nose, the gap presenting a tortuous path for bacteria after sterilization.

13. A medical connector, comprising:

an elongate tubular body having a proximal and a distal end, and a central lumen extending axially therethrough, said proximal end adapted for receiving a flexible tubular conduit;

a hub on the tubular body, movable between a distal position in which the hub is rotatable about the tubular body, an intermediate position in which the hub is rotationally locked with respect to the tubular body, and a proximal position in which the hub is displaced along the tubular conduit in a proximal direction from the tubular body;

a first stop on the tubular body; and a complementary second stop on the hub, wherein said first and second tapered stops contact each other when the hub is in the distal position to prevent said first stop from advancing distally past said second stop, wherein said tubular body further comprises a radially outwardly extending projection and said hub further comprises an axially extending channel on the radially interior surface thereof, for receiving said projection, such that the hub is rotationally locked with respect to the tubular body when the projection is positioned within the channel, and wherein the hub remains axially movable with respect to the tubular body, wherein said projection comprises an axially extending spline, wherein said hub comprises at least two radially inwardly directed ribs surrounding said channel and said spline has a wide portion having a circumferential width substantially equal to the circumferential width of said channel between said ribs, wherein there is a first wide portion formed on the proximal end of said spline, and a second wide portion formed on the distal end of said spline, and said spline has a narrow central portion, and wherein said first and second wide portions extend in opposite circumferential directions from said narrow central portion to interfere with said ribs when said hub is moved axially along said tubular body.

14. A connector as in claim 13, wherein said spline tapers axially in the distal direction to provide a distally directed point.

15. A connector as in claim 13, wherein said wide portion is formed on the proximal end of.

16. A connector as in claim 13, further comprising a ridge on the tubular body for indicating when the hub is in the proximal position and rotationally locked to the tubular body.

17. A connector as in claim 13, wherein said first wide portion extends perpendicularly from said narrow central portion to define a barrier to proximal movement of one of said ribs unless said hub is manually rotated with respect to said tubular body.

18. A connector as in claim 17, further comprising a bump on the tubular body for interfering with said one rib to provide a tactile feedback when said hub is manually rotated with respect to said tubular body.

19. A connector as in claim 13, wherein said second wide portion extends at an angle from said narrow central portion so that said hub can be advanced over said tubular body from a proximal end thereof and said hub is automatically rotated as one of said ribs cams around said second wide portion.

20. A connector as in claim 13, further comprising ISO threads on the interior surface of the hub, for engaging a complementary luer connector.

21. A connector as in claim 13, wherein said first stop comprises an annular surface surrounding said tubular body, said surface inclined radially outwardly in the distal direction, and said second stop also inclines radially outwardly in the distal direction.

22. A connector as in claim 21, wherein each of said first and said second stops incline radially outwardly in the distal direction at an angle within the range of about 0.5° to 60° with respect to the longitudinal axis of the tubular body.

23. A connector as in claim 22, wherein each of said first and said second stops incline radially outwardly in the distal direction at an angle within the range of about 30° to 60° with respect to the longitudinal axis of the tubular body.

24. A connector as in claim 21, wherein said first stop has a proximal taper which inclines radially outwardly in the distal direction at an angle within the range of about 30° to 60° with respect to the longitudinal axis of the tubular body, and a distal taper which inclines radially outwardly in the distal direction at an angle within the range of about 0.5° to 7° with respect to the longitudinal axis of the tubular body.

25. A connector as in claim 13, wherein said hub must be inserted onto said tubular body from a proximal end thereof for said first stop to contact said second stop.

26. A connector as in claim 13, further comprising at least one ridge on the tubular body for indicating when the hub is in the intermediate position in which the hub is rotationally locked with respect to the tubular body.

27. A connector as in claim 13, wherein said tubular body further comprises a distal tapered nose, and wherein said connector further comprises a cap adapted for fitting over and protecting said nose, said cap including a plurality of projections which are adapted for forming a gap between the cap and the tubular body when the cap is placed over the tapered nose, the gap presenting a tortuous path for bacteria after sterilization.

28. A medical connector, comprising:

an elongate tubular body having a proximal and a distal end, and a central lumen extending axially therethrough, said body comprising a proximal tubular section for attaching to a medical supply line, a distal tapered nose, and a shoulder disposed therebetween, said shoulder comprising an annular surface extending from said proximal tubular section, said surface inclined radially outwardly in the distal direction and terminating in a distally facing wall;

a hub on the tubular body, movable between a distal position in which the hub is rotatable about the tubular body, and a proximal position in which the hub is rotationally locked with respect to the tubular body, and said hub comprises ISO threads on the interior surface thereof, for engaging a complementary luer connector; and a protective cap to protect said nose defined by a closed-ended tubular body having a proximal engagement tube portion with an interior wall tapered at approximately the same angle as the tapered nose, said engagement tube portion includes a series of outwardly directed ribs provided to frictionally engage the inwardly directed threads on the hub, wherein said cap includes a plurality of projections formed on a proximal end of said engagement tube portion which contact said wall to create a gap between the protector cap and the tubular body for ease of priming the device when the cap is in place, the gap presenting a tortuous path for bacteria after sterilization.

29. A medical connector as in claim 28, wherein said ribs terminate in distal ramped surfaces and are rounded in cross-section.

30. A medical connector as in claim 28, wherein said threads have a predetermined pitch and said ribs are spaced apart circumferentially around said engagement tube portion so that all the ribs contact the same number of said threads in any rotational orientation of said cap when said cap is fully inserted over said nose so as to provide a consistent frictional engagement therebetween.

31. A connector as in claim 28, further comprising at least one ridge on the tubular body for indicating when the hub is in the proximal position in which the hub is rotationally locked with respect to the tubular body.

32. A connector as in claim 28, wherein said tubular body further includes at least one radially outwardly extending projection, which comprises an axially extending spline, and
wherein said spline comprises a plurality of wide portions extending in opposite circumferential directions.

* * * * *